(12) United States Patent (10) Patent No.: US 8,974,374 B2
Schostek et al. (45) Date of Patent: Mar. 10, 2015

(54) SURGICAL MANIPULATOR

(75) Inventors: Sebastian Schostek, Tubingen (DE); Rudiger Proβt, Stuttgart (DE); Fabian Rieber, Stuttgart (DE); Marc Oliver Schurr, Tubingen (DE)

(73) Assignee: Novineon Healthcare Technology Partners GmbH, Tubingen (DE)

( * ) Notice: Subject to any disclaimer, the term of this patent is extended or adjusted under 35 U.S.C. 154(b) by 528 days.

(21) Appl. No.: 12/860,767

(22) Filed: Aug. 20, 2010

(65) Prior Publication Data

US 2011/0152615 A1 Jun. 23, 2011

(30) Foreign Application Priority Data

Aug. 21, 2009 (EP) ..................................... 09010776

(51) Int. Cl.
*A61B 1/00* (2006.01)
*A61B 1/04* (2006.01)
*A61B 19/00* (2006.01)
*A61B 17/00* (2006.01)
*A61B 17/29* (2006.01)

(52) U.S. Cl.
CPC ... *A61B 19/2203* (2013.01); *A61B 2017/00477* (2013.01); *A61B 2017/2906* (2013.01); *A61B 2019/2249* (2013.01); *A61B 2019/2215* (2013.01)
USPC ........................................................ 600/118

(58) Field of Classification Search
CPC ................ A61B 19/2203; A61B 2017/00477; A61B 2017/2906; A61B 2019/2215; A61B 2019/2249
USPC .................. 600/114, 117–118, 204; 606/130
See application file for complete search history.

(56) References Cited

U.S. PATENT DOCUMENTS

| | | | |
|---|---|---|---|
| 5,876,325 A | 3/1999 | Mizuno et al. | |
| 2003/0114731 A1* | 6/2003 | Cadeddu et al. | 600/114 |
| 2005/0096502 A1 | 5/2005 | Khalili | |
| 2007/0255100 A1* | 11/2007 | Barlow et al. | 600/114 |
| 2007/0255273 A1 | 11/2007 | Fernandez | |
| 2008/0058835 A1* | 3/2008 | Farritor et al. | 606/130 |
| 2008/0221591 A1* | 9/2008 | Farritor et al. | 606/130 |
| 2009/0048612 A1* | 2/2009 | Farritor et al. | 606/130 |
| 2009/0054909 A1* | 2/2009 | Farritor et al. | 606/130 |

(Continued)

FOREIGN PATENT DOCUMENTS

WO 2008/103212 A2 8/2008
WO WO 2008/103212 8/2008

OTHER PUBLICATIONS

European Patent Office, Communication pursuant to Article 94(3) EPC, for European Patent Application 09010776.4, Mar. 27, 2012, 1pg.

(Continued)

*Primary Examiner* — John P Leubecker
*Assistant Examiner* — Arnaldo Torres Diaz
(74) *Attorney, Agent, or Firm* — TechLaw LLP

(57) ABSTRACT

A surgical manipulator includes an intracorporeal unit that is completely arrangeable within a body cavity and that includes a coupling member and an effector. An extracorporeal unit includes a manipulator to manipulate at least the effector, and a connecting unit for connecting the intracorporeal unit to the extracorporeal unit when the intracorporeal unit is arranged within the body cavity and for transferring manipulating activities from the extracorporeal unit to the intracorporeal unit.

27 Claims, 27 Drawing Sheets

(56) References Cited

U.S. PATENT DOCUMENTS

| | | | |
|---|---|---|---|
| 2009/0069821 A1* | 3/2009 | Farritor et al. | 606/130 |
| 2009/0076536 A1 | 3/2009 | Rentschler et al. | |
| 2009/0082627 A1* | 3/2009 | Karasawa et al. | 600/118 |
| 2009/0171373 A1* | 7/2009 | Farritor et al. | 606/130 |
| 2011/0087236 A1* | 4/2011 | Stokes et al. | 606/130 |

OTHER PUBLICATIONS

European Patent Office, Communication pursuant to Article 70(2) and reference to Rule 39(1) EPC, for European Patent Application 09010776.4, Feb. 28, 2011, 1pg.

European Patent Office, Communication—Extended European Search Report for European Patent Application 09010776.4, Mar. 23, 2010, 6pgs.

* cited by examiner

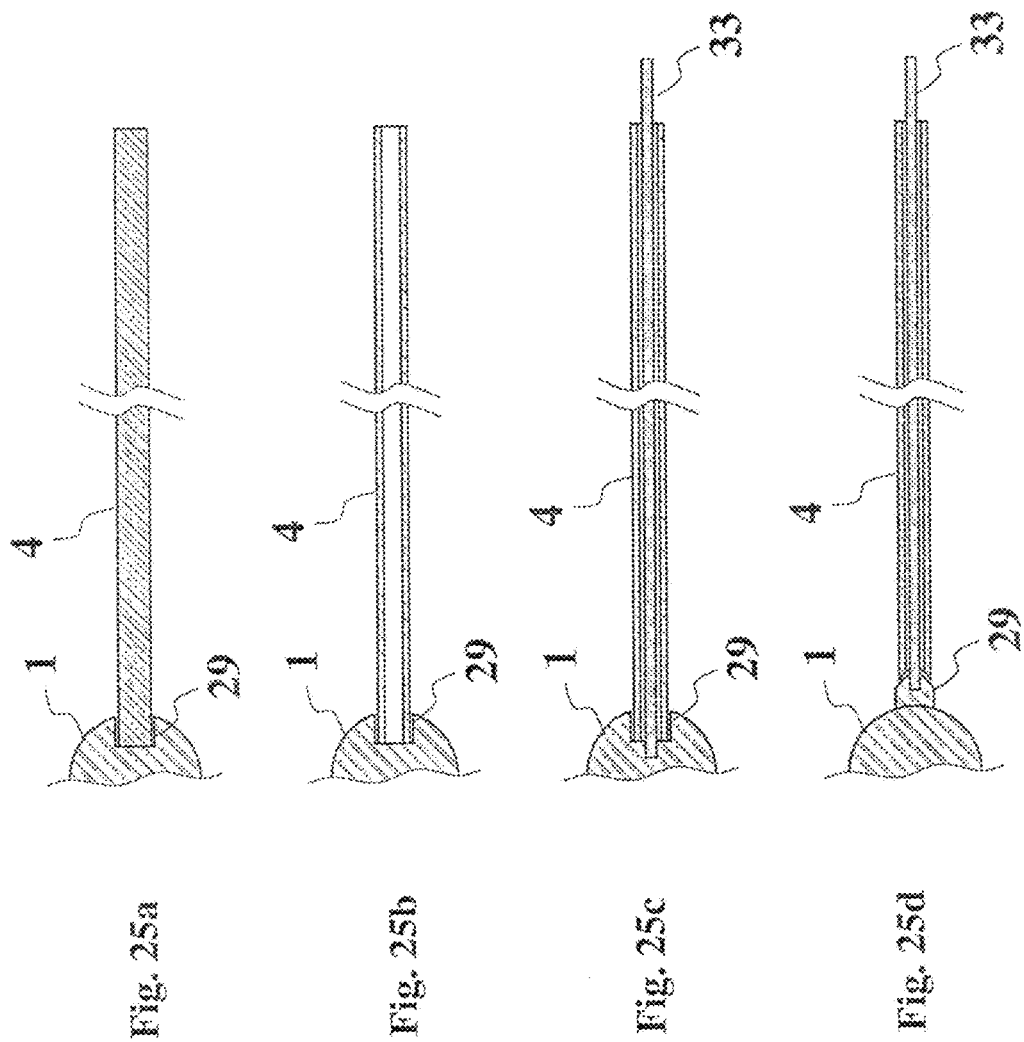

SURGICAL MANIPULATOR

TECHNICAL FIELD

The present invention relates to the field of endoscopic surgery and, in particular, to devices and systems for controlling intracorporeal surgical devices with extracorporeal control mechanisms.

BACKGROUND

In surgery the trend goes to a minimization of the access trauma in surgical operations (minimally invasive surgery). Moreover, further complex procedures with minimally invasive processes are performed. Since the required surgical instruments for the complex procedures have to be introduced and removed through incisions, the minimization of the size of the incisions is limited by the size of the surgical instruments to be inserted. Further, access ports (trocars) are required for introducing a surgical instrument into the body and removing it therefrom and simultaneously maintaining an interior pressure of the body (valve function of the trocars). These trocars even enlarge the size of the incisions.

In U.S. Pat. No. 5,876,325, a surgical manipulator system is disclosed comprising at least one surgical manipulator which holds a surgical device for performing a desired operation and at least one controlling device for controlling the surgical manipulator. Further, a detector is provided for detecting a geometrical relationship between the surgical manipulator and controlling device, or for detecting a geometrical relationship between the surgical manipulator and another surgical manipulator. Additionally, a drive controller for controlling the surgical manipulator in response to the controlling device and the detector is provided. However, the surgical manipulator system according to U.S. Pat. No. 5,876,325 is for operating on a patient in conventional form. That is, the disclosed surgical manipulator system is not applicable for minimally invasive surgery.

International Patent Application WO 2008/103212 A2 discloses a surgical system for minimally invasive surgery comprising a console having a display and at least one manipulator arm, a robotic device comprising a camera, where the robotic device is configured to be positioned completely within a body cavity of a patient. The robotic device is connected to the console via an electrical wire transmitting signals and energy from the console to the robotic device. The robotic device is introduced into the patient's body through a natural body orifice and the robotic device is arranged relative to the console via a magnetic device. The arrangement of the manipulator arm at the console and the arrangement of the robotic device relative to the console is for giving the operator the feeling of a direct view into the patient's body. With such a surgical system, incisions into the patient's body can be completely prevented. However, since the robotic device is arranged relative to the console by a magnetic device (i.e., the console and the robotic device comprise magnets), the robotic device always abuts against the inner wall surface of the body cavity. That is, the surgical system according to International Patent Application WO 2008/103212 A2 does not allow the robotic device to be moved towards the center of a patient's body. Further, in case of an obese patient, the magnetic means does not have the ability to fix the robotic device in position.

In U.S. Patent Application No. 2009/0076536 A1, it is disclosed to fix the robotic device to the abdomen wall by means of pins or needles which are pierced through the abdomen wall. In the case where the robotic device is fixed to the abdomen wall by one single pin or needle, the robotic device is able to be rotated around the point of attachment of the needle to the robotic device. In the case where the robotic device is fixed to the abdomen wall by two needles or pins, the position and attitude of the robotic device may be controlled via the needles or pins. Energy and signals for controlling the manipulation of the robotic device are transmitted from outside the patient's body to the robotic device via a cable which is introduced into the body cavity through a natural body orifice together with the robotic device.

In the above arrangements the problem inheres that at least a cable passes through the natural body orifice of the patient's body even in the case where the robotic device is already provided within the patient's body. Further, the signal and energy cable may interfere with the manipulator arms of the robotic device when a surgeon operates by means of the robotic device.

SUMMARY

A surgical manipulator is provided comprising an intercorporeal unit, forming a mechanically moveable single module, being completely arrangeable within a body cavity and having a central member (coupling member) and an effector, for example at least one manipulator arm, an extracorporeal unit and a connecting unit for detachably mechanically connecting the intracorporeal unit to the extracorporeal unit when the intracorporeal unit is arranged within the body cavity. The connecting unit comprising at least two single shafts distanced from each other is adapted to be partly introduced into the body cavity through at least two punctures in the body wall (each shaft creates its own puncture in the body wall). The connecting unit is further adapted to transmit control signals (electrical, mechanical, optical etc.) from the extracorporeal unit to the intracorporeal unit.

With this arrangement, no additional signal cable is needed for transmitting the control signals from outside the patient's body to the intracorporeal unit. Therefore, the manipulator arm of the surgical manipulator may no more interfere with such a signal cable.

Since the connecting unit is not removed during the operation, trocars are not required for maintaining the body inner pressure. This also further reduces the access trauma. Additionally, postoperative pain and the risk of complications are minimized for the patient, since the incisions created by the plurality of separate shafts are small sized, respectively, compared to one single incision for introducing a single trocar.

According to another aspect of the invention a conveyor for conveying said intracorporeal unit into the body cavity separately from the connecting unit and a guide is provided for bringing said intracorporeal unit together with said connecting unit within the body cavity. By separating (disconnecting) the intracorporeal unit and the connecting unit, the intracorporeal unit can be individually and separately positioned within a body cavity by using a natural passage, for example the esophagus, and the connecting unit can enter the body cavity via incision(s) in the body wall. Inside the body cavity both units have to be interconnected for which the guide is arranged.

This system minimizes the size of the incisions in the body wall to the size of the connecting unit which is generally smaller in diameter than the intracorporeal unit.

According to a further aspect of the invention, the connecting unit of the surgical manipulator is adapted to transmit energy from the extracorporeal unit to the intracorporeal unit.

Since there is a direct mechanical connection between the extracorporeal unit and the intracorporeal unit via the connecting unit, the effector, for example the at least one manipulator arm of the intracorporeal unit, may be directly mechanically controlled without transmitting further energy from the extracorporeal unit to the intracorporeal unit. However, according to this aspect of the invention, additionally to the transmission of direct mechanically control signals, energy may be transmitted from the extracorporeal unit to the intracorporeal unit via the connecting unit in order to drive actuators provided in the intracorporeal unit. It is contemplated that part of the control of the intracorporeal unit is carried out by directly transmitting mechanical control signals from the extracorporeal unit to the intracorporeal unit and simultaneously electrical signals are transmitted from the extracorporeal unit to the intracorporeal unit via the connecting unit for driving actuators provided in the intracorporeal unit. It is further contemplated that sensors are provided in the intracorporeal unit which generate electrical signals to be transmitted from the intracorporeal unit to the extracorporeal unit via the connecting unit.

According to a further aspect of the present invention, the at least one manipulator arm comprises a plurality of limbs and joints.

In this application, the term "limb" refers to a segment between two joints. That is, a manipulator arm comprises of a succession of limbs and joints. Each limb of one manipulator arm is movable relative to each adjacent limb with at least one degree of freedom.

According to a further aspect of the surgical manipulator system, the joints include swivel joints, torsion joints and/or ball and socket joints.

These kinds of joints allow the limbs of one manipulator arm to be moved and swivelled in several directions. The distal end of the manipulator arm (relative to the central member) can be brought into any required position.

According to a further aspect of the surgical manipulator system, the at least one manipulator arm comprises at its distal end a surgical end effector.

With the surgical end effector, body tissue may be gripped or cut or otherwise dealt. In the case where two manipulator arms are provided to the intracorporeal unit, one end effector may be a forceps and the other end effector may be a scalpel. Then, tissue gripped by the forceps may be cut by the scalpel. However, any known medical tool may be provided as an end effector.

According to a further aspect of the surgical manipulator system, the surgical end effector may be detachably and replaceably mounted to the respective manipulator arm.

With this special arrangement, the surgical end effector may be adapted to the actual operation before being introduced into the patient's body or, further preferably, the intracorporeal unit comprises some kind of magazine such that the surgical end effector may be replaced during operation within the patient's body. With this arrangement, a plurality of tools can be provided within the patient's body. It is also contemplated that no surgical end effector is provided to the manipulator arms during introduction of the intracorporeal unit into the patient's body. After insertion thereof, each manipulator arm gathers a corresponding tool out of a tool magazine provided to the intracorporeal unit. With this arrangement, introduction of the intracorporeal unit into the patient's body may be simplified. Otherwise, in case a blade is provided to a manipulator arm, body tissue may be accidentally injured during insertion of the intracorporeal unit into the patient's body. Further preferable, end caps may be provided to the manipulator arms in such a case which are specifically adapted for ease of introduction of the intracorporeal unit.

According to a further aspect of the present invention, the at least one surgical end effector is movable relative to the central member with plural degrees of freedom.

That is, the surgical end effector is able to be moved in various directions or to be rotated or swivelled in various directions. According to one aspect of the present invention, the degrees of freedom of the surgical end effector correspond to the degrees of freedom of a human hand relative to the shoulder. That is, the manipulator arm comprises swivel joints and torsion joints similar to the human arm. Further, these movements may be mechanically controlled and further movements of the manipulator arm may be effected by actuators.

According to a further aspect of the surgical manipulator system, the connecting unit comprises at least two connecting members which are to be passed through the body wall through separate punctures and being connectable to the intracorporeal unit.

With such connecting members, the size of each puncture can be further minimized such that wound healing is improved. For example, two manipulator arms are provided to the intracorporeal unit. Then, two connecting members may be provided such that each connecting member is able to transmit the control signals (at least the mechanical control signals) for the respective manipulator arm from the extracorporeal unit to the intracorporeal unit. In case sensors or other entities are provided to the intracorporeal unit, a third connecting member may be provided for transmission of the signals thereof from or to the intracorporeal unit.

According to a further aspect of the surgical manipulator system, the at least one connecting member of the connecting unit is connectable to the central member and/or the at least one manipulator arm of the intracorporeal unit.

In the case where the connecting member is connected to the central member, control signals transmitted from the extracorporeal unit to the intracorporeal unit are forwarded to the manipulator arm. Where the connecting member is directly connected to the manipulator arm, the manipulator arm may also be controlled by movement of the connecting member. Where one connecting member is connected to the central member and another connecting member is connected to a first limb of a manipulator arm (i.e., a limb of the manipulator arm which is directly pivoted to the central member), by shifting the one connecting member relative to the other connecting member, the manipulator arm is swivelled relative to the central member. Depending on the arrangement of the connecting members and the extracorporeal unit, further movements of a manipulator arm may be controlled in a similar way.

According to a further aspect of the surgical manipulator system, the intracorporeal unit comprises a monitor for monitoring the sphere of action of the at least one manipulator arm.

Since the surgeon is not able to directly look into the patient's body, because the surgical manipulator system is used in minimally invasive surgery, the monitor allows the surgeon to monitor the interior of the human body. Usually, the monitor is a normal camera or a stereoscopic camera which may also be focusable. The signals of the monitor may be transmitted through a connecting member that also transmits control signals for the manipulator arm(s). Alternatively, these signals are transmitted through a separate connecting member. Moreover, the camera may also be positioned on the tip end of a connecting member. Then, the connecting member may pierce through the intracorporeal unit thereby making connection to the intracorporeal unit and the camera being exposed to the sphere of action of the manipulator arm(s). With this arrangement, a transmission of the camera signals from the intracorporeal unit to the connecting member is not required, thus leading to reduced complexity of the connection of the respective connecting member to the intracorporeal unit. Further alternatively, the camera may also be inserted into the human body separately from the surgical manipulator system.

According to a further aspect of the surgical manipulator system, the intracorporeal unit further comprises an illuminator for illuminating the sphere of action of the at least one manipulator arm.

With such an illuminator, since it is very dark within the human body, the sphere of action of the at least one manipulator arm may be illuminated so that the surgeon can orientate in the human body. According to an alternative, the illuminator may be inserted into the human body in a similar way to the camera. That is, the illuminator may also be provided to a tip end of a connecting member which pierces through the intracorporeal unit.

Then, a light conductor may also be used as an illuminator. This provides the further advantage that no electricity has to be transmitted into the patient's body for illumination and no heat is generated due to conversion of electricity into light. The illuminator may be provided to the central member or one or more manipulating arm(s). It is also contemplated that a connecting member comprises an illuminator at a tip end thereof and a ball joint close to the illuminator. Then, the concerned connecting member may pierce through a limb of a manipulator arm. By provision of the ball joint in such a way that it is positioned close to the surface of the concerned limb outside of the limb ("behind" the limb of the manipulator arm), movement of the limb may be effected by shifting this connecting member relative to another connecting member without damaging the connecting member and without the connecting member impeding the movement. That is because the ball joint allows a bending of the connecting member due to the swivelling of the concerned limb.

Further alternatively, the illuminator may be introduced into the patient's body separately from the surgical manipulator system. The illuminator may comprise any known light source, for example a light emitting diode (LED). A LED has the advantage that heat is hardly generated within the patient's body. Alternatively, as already indicated above, the light is not generated within the patient's body but is generated outside and is transmitted via a light conductor as photonic energy into the patient's body.

According to another aspect of the surgical manipulator system, the extracorporeal unit comprises at least one manual handle via which the at least one manipulator arm and/or the at least one surgical end effector being controllable.

The movements of the manual handle may be transmitted mechanically through the connecting units to the manipulator arm and/or the end effector. In an alternative, the movements of the manual handle may be transmitted into electrical signals which are transmitted into the intracorporeal unit and then retransmitted into physical movement of the manipulator arm and/or the at least one surgical end effector. In the latter case, a surveillance device may be provided to the extracorporeal unit monitoring the movements of the handle. In case a movement is judged to be dangerous to the patient, the surveillance device may modify the control signals in such a way that the patient is not harmed. For example, too fast movements of the handle are detected and slowed down since too fast movements of a manipulator arm and a surgical end effector, respectively, may injure organs or tissue within the patient's body. The manual handle may be similar to a handle of a known medical grasping device. However, the handle may also be more complex and provide more control signals, i.e. more degrees of freedom, for control of the concerned manipulator arm and surgical end effector, respectively.

According to another aspect of the surgical manipulator system, the extracorporeal unit further comprises at least one actuator via which the at least one manipulator arm and/or the at least one surgical end effector being controllable.

With such an actuator, the control may be carried out by some sort of computer program or the control may be carried out from a place remote to the place of operation. That is, this aspect allows some sort of control-by-wire operation.

According to another aspect, the surgical manipulator system comprises at least one manual handle, at least one actuator and a transmitting unit for transforming the inputs of the at least one handle into signals, for combining these signals with the signals of the at least one actuator and for transmitting the combined signals through the connecting unit through the intracorporeal unit.

With the above arrangement, the at least one manipulator arm or the at least one surgical end effector may partly be controlled by direct movement of the manual handle and by signals generated by the actuator. This is specifically favourable in case the manipulator arm is able to move with more degrees of freedom than the manual handle provides or some of the movements are hard to input through the concerned handle.

According to another aspect of the surgical manipulator system, it comprises a bearing device bearing the connecting unit in such a way that the connecting unit is able to be rotated and/or axially shifted relative thereto, wherein the position of the bearing device relatively to the concerned body cavity is adjustable via a holding arm which is fixable via a fixing means.

With such a bearing device, the extracorporeal unit may be positioned relative to the patient's body such that the accuracy of the surgical manipulator system may be further improved.

In principle, movements of the limbs of the manipulator arms of the intracorporeal unit may either be effected by actuators integrated into the manipulator arms, wherein energy and control signals are supplied via the connecting unit, by actuators integrated into the extracorporeal unit, wherein mechanical energy is transmitted via the connecting unit, or by direct manual control at the extracorporeal unit, wherein also mechanical energy is transmitted via the connecting unit.

Furthermore, the extracorporeal unit may comprise at least one manual handle, at least one actuator, and a transmitting unit for transforming the inputs of the at least one handle into signals, for combining these signals with the signals of the at least one actuator, and for transmitting the combined signals through the connecting unit to the intracorporeal unit.

In some cases it is advantageous to arrange a bearing device bearing the connecting unit in such a way that the connecting unit is able to be rotated and/or axially shifted relative thereto, wherein the position of the bearing device relatively to the concerned body cavity is adjustable via a holding arm which is fixable via a fixing means.

Finally, the conveyor can be an endoscope and of a gastric type.

These and other features of various embodiments, together with the organization and manner of operation thereof, will become apparent from the following detailed description when taken in conjunction with the accompanying drawings, in which like reference numerals are used to refer to like parts throughout.

BRIEF DESCRIPTION OF THE DRAWINGS

Provided embodiments are illustrated by way of example, and not of limitation, in the figures of the accompanying drawings in which:

FIGS. 25a to 25g show different designs for couplings between the intracorporeal unit and the connecting unit.

DETAILED DESCRIPTION

In the following, a first embodiment of the surgical manipulator is explained by reference to FIGS. 1 to 11, 15, 17, 18, 22 and 23.

Figure 1:
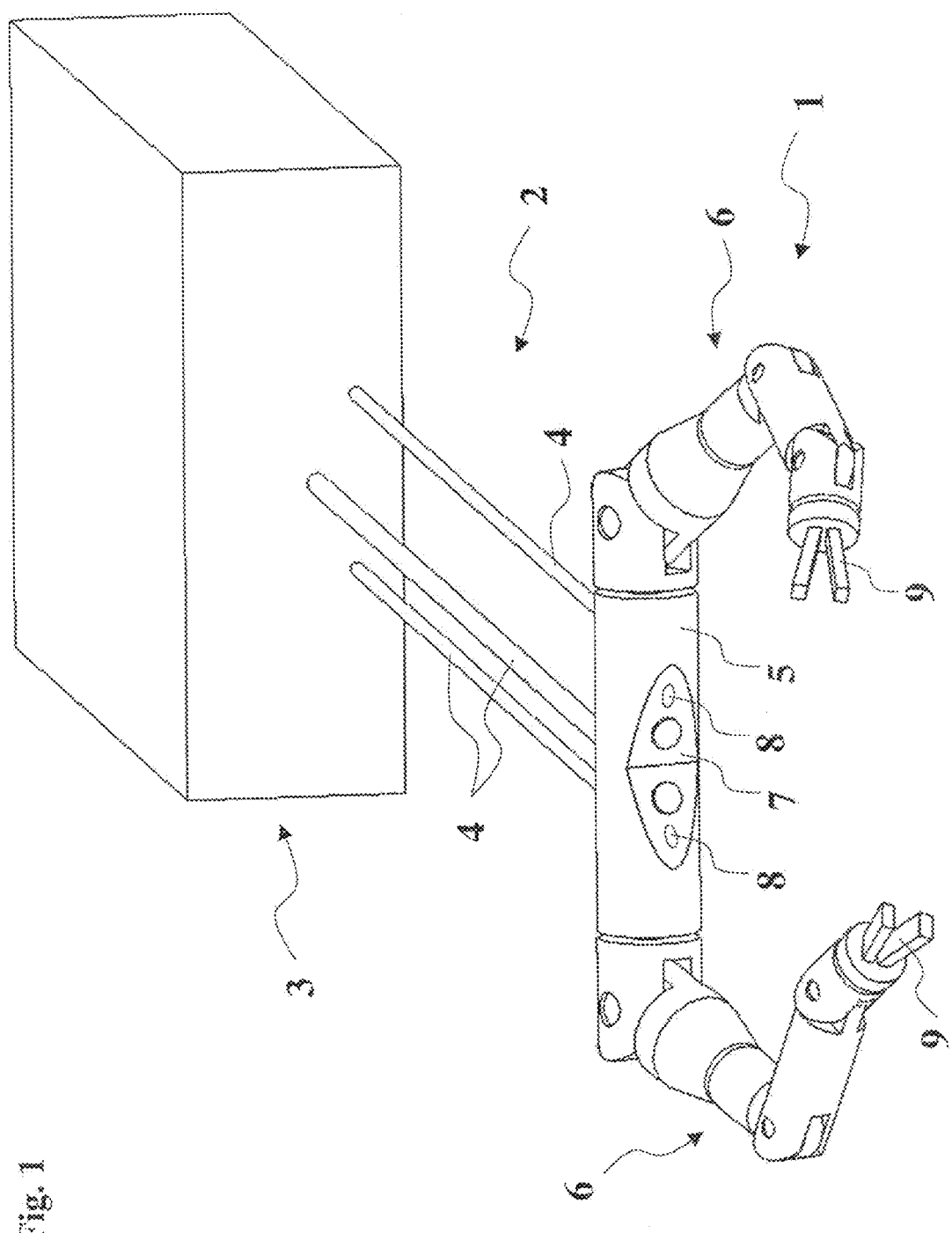
FIG. 1 is a view showing a first embodiment of the surgical manipulator according to the present invention.
Figure 2:
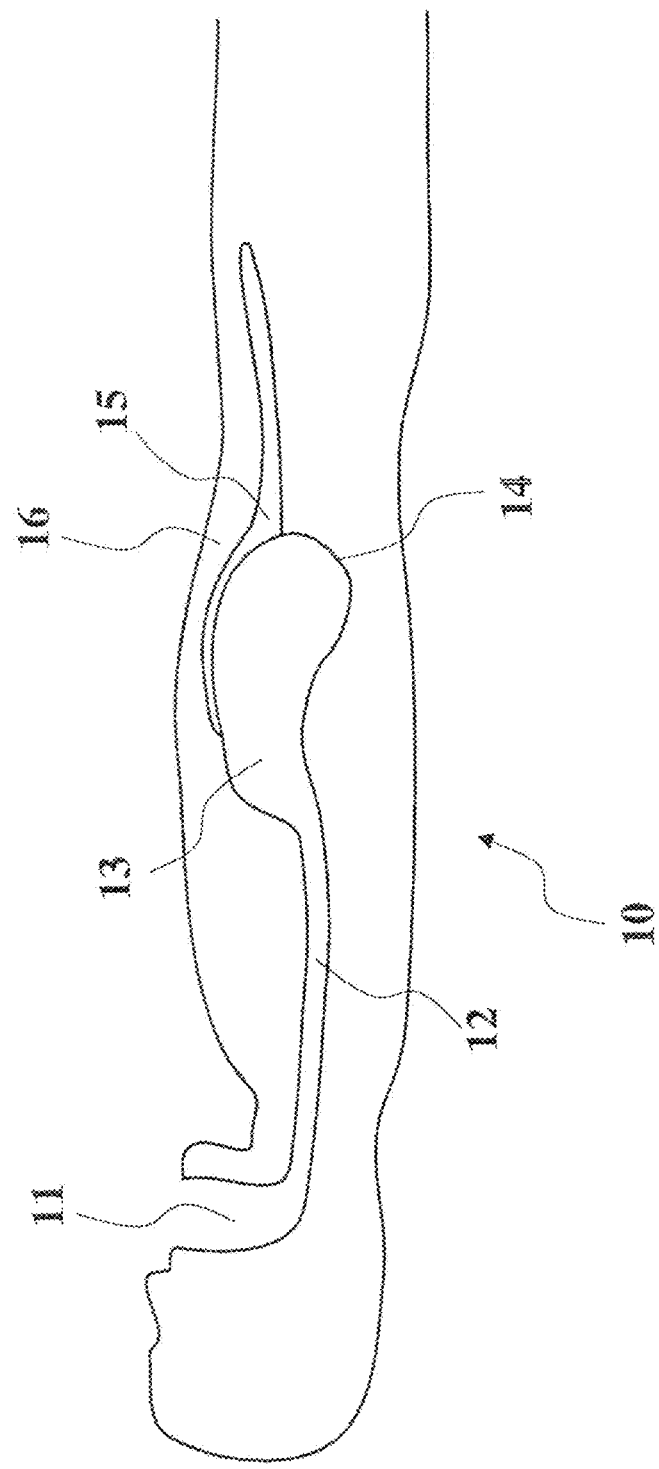
FIG. 2 is view showing a schematic longitudinal section through a patient's body.
Figure 3:
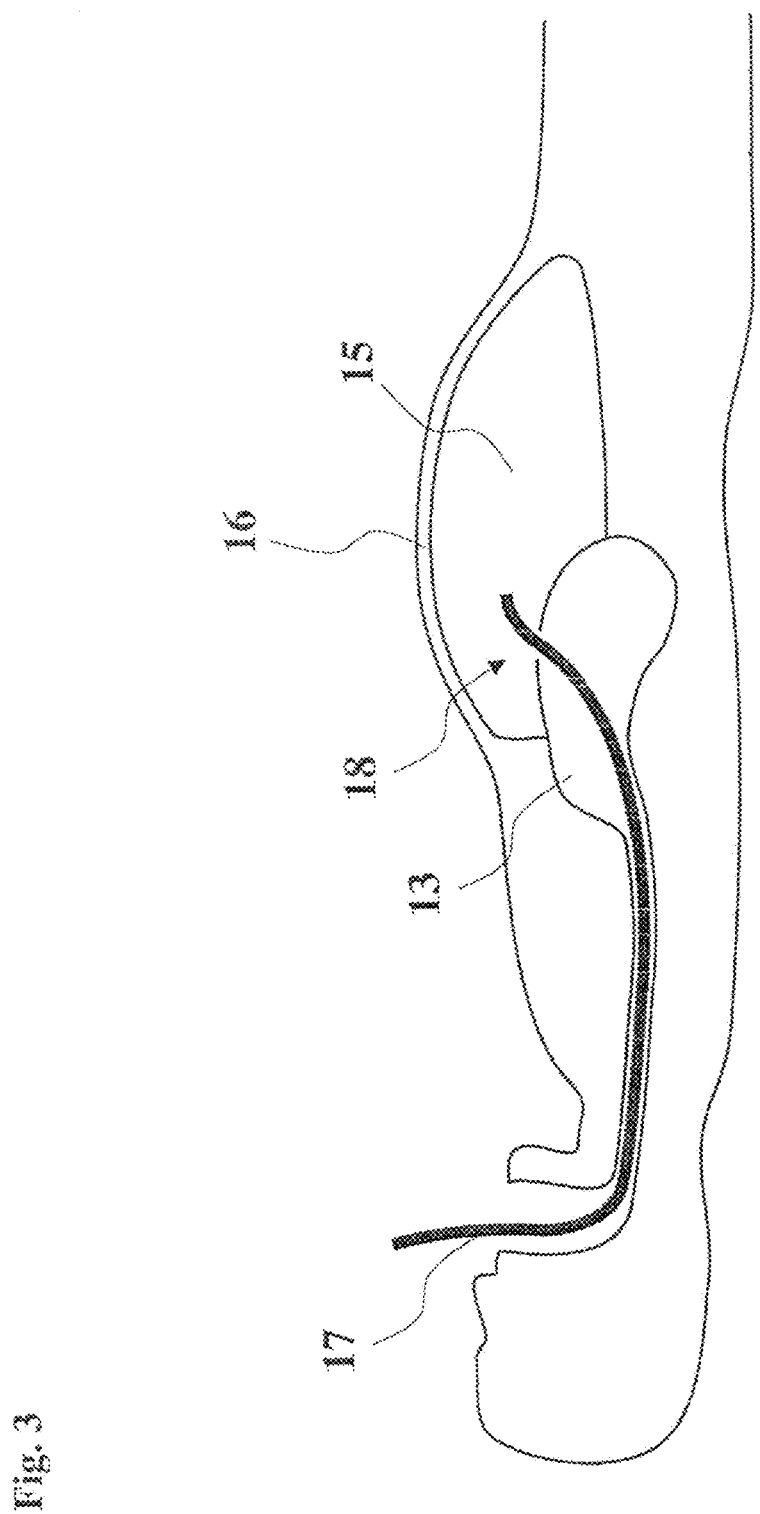
FIG. 3 is a view according to FIG. 2, wherein a flexible endoscope is inserted through the patient's esophagus and a puncture in the stomach wall into the abdomen.
Figure 4:
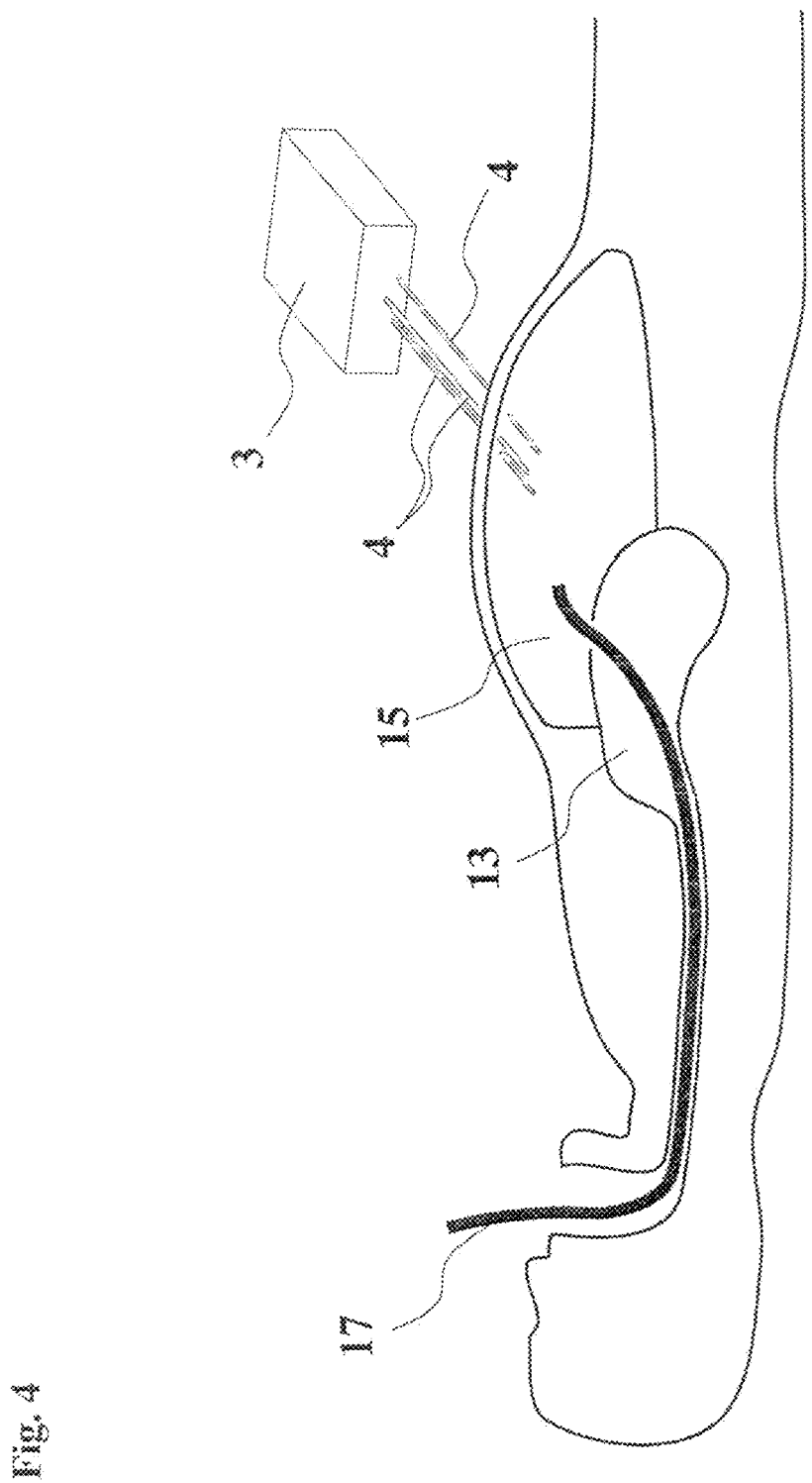
FIG. 4 is a view according to FIGS. 2 and 3, wherein a tip end of a connecting unit of a surgical manipulator is inserted into the patient's abdomen through the abdomen wall.
Figure 5:
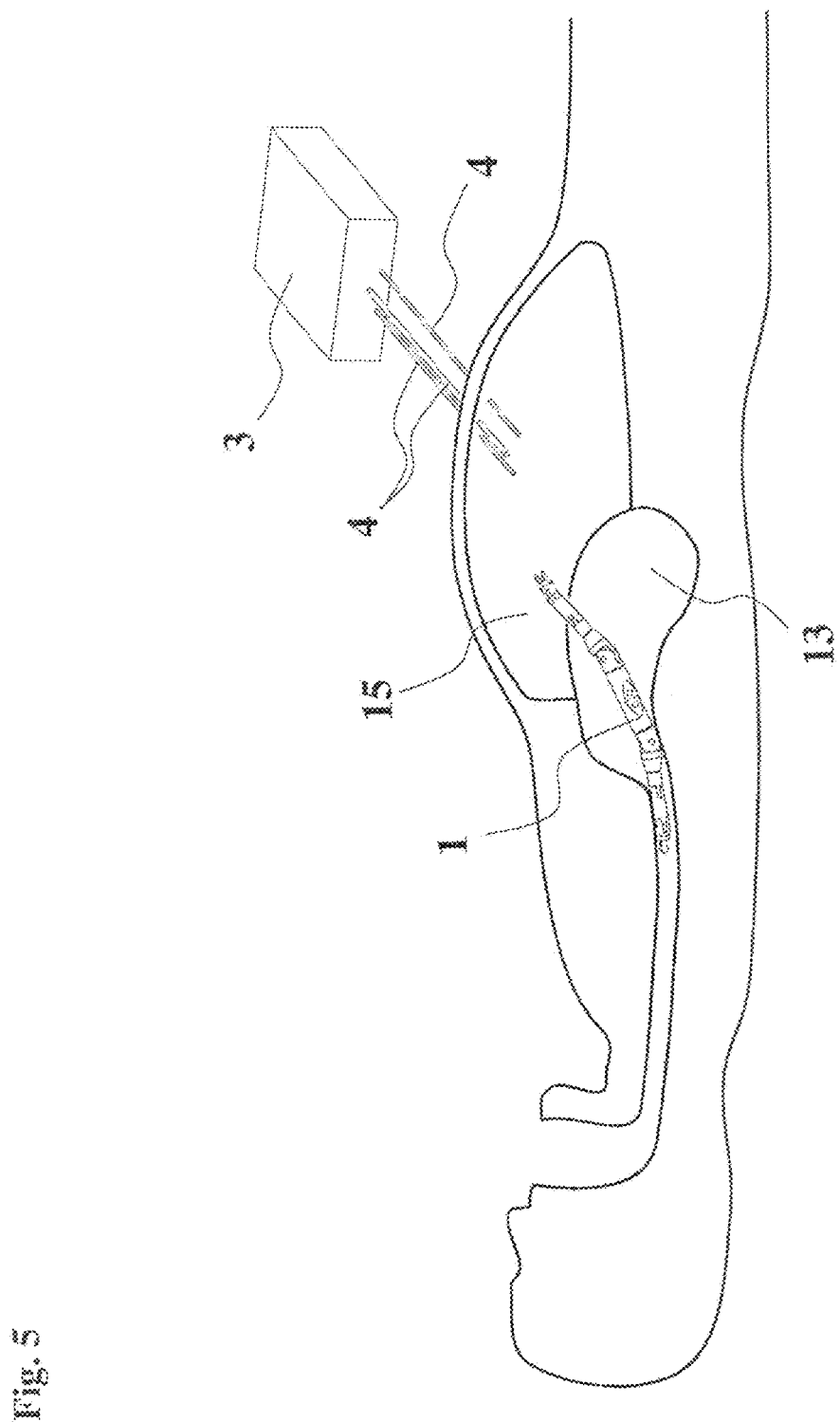
FIG. 5 is a view showing schematically an introduction of the intracorporeal unit into the patient's abdomen through the puncture in the stomach wall.
Figure 6:
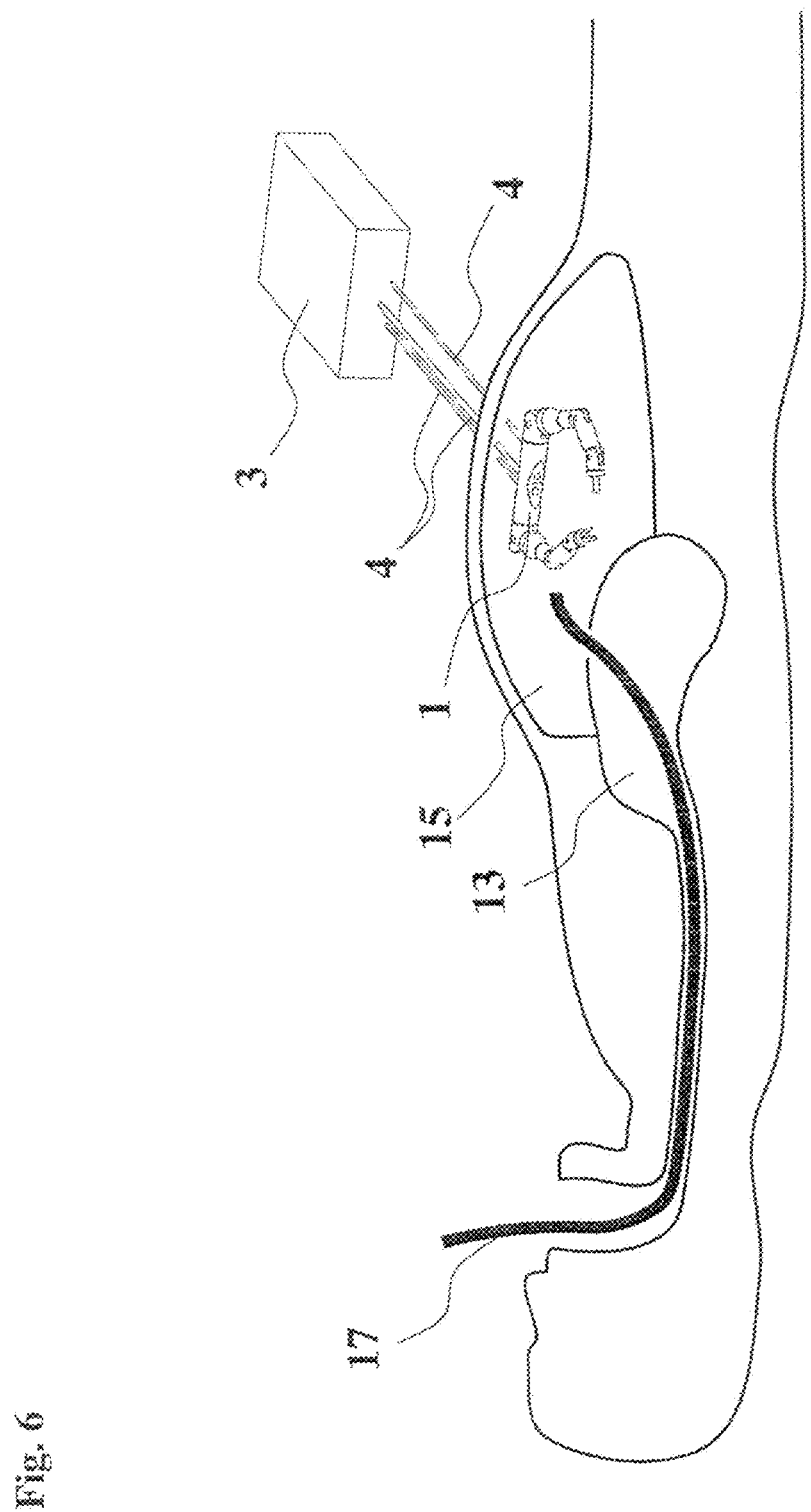
FIG. 6 is a view according to FIG. 5, wherein a flexible endoscope is inserted through the esophagus and the stomach into the abdomen and wherein the intracorporeal unit is mounted to the connecting unit.
Figure 7:
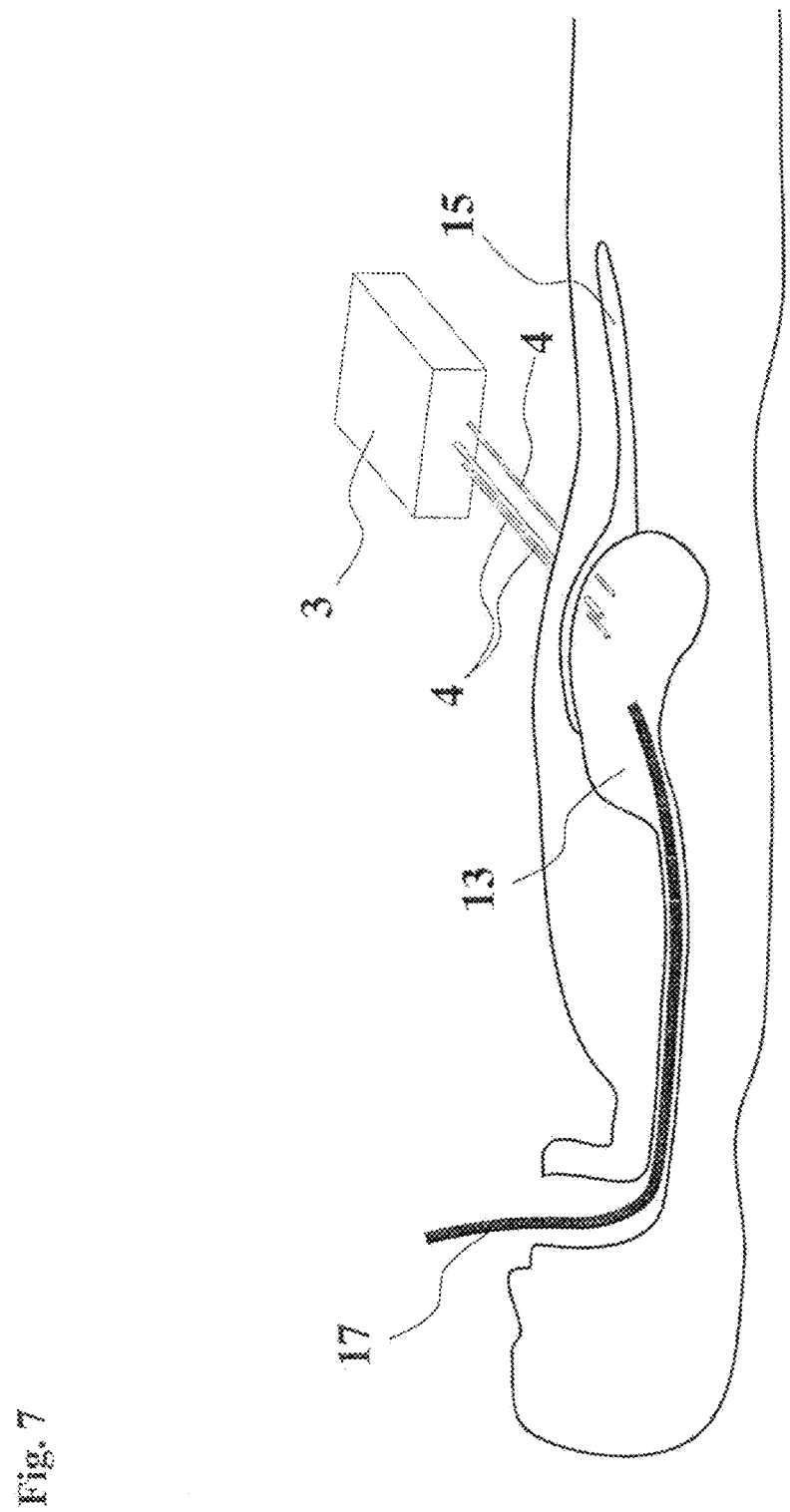
FIG. 7 is a view similar to FIG. 4 showing schematically a longitudinal section through a patient's body, wherein a flexible endoscope is inserted through the esophagus into the stomach and wherein a tip end of a connecting unit of the surgical manipulator is inserted into the patient's stomach through the abdomen wall and the stomach wall.
Figure 8:
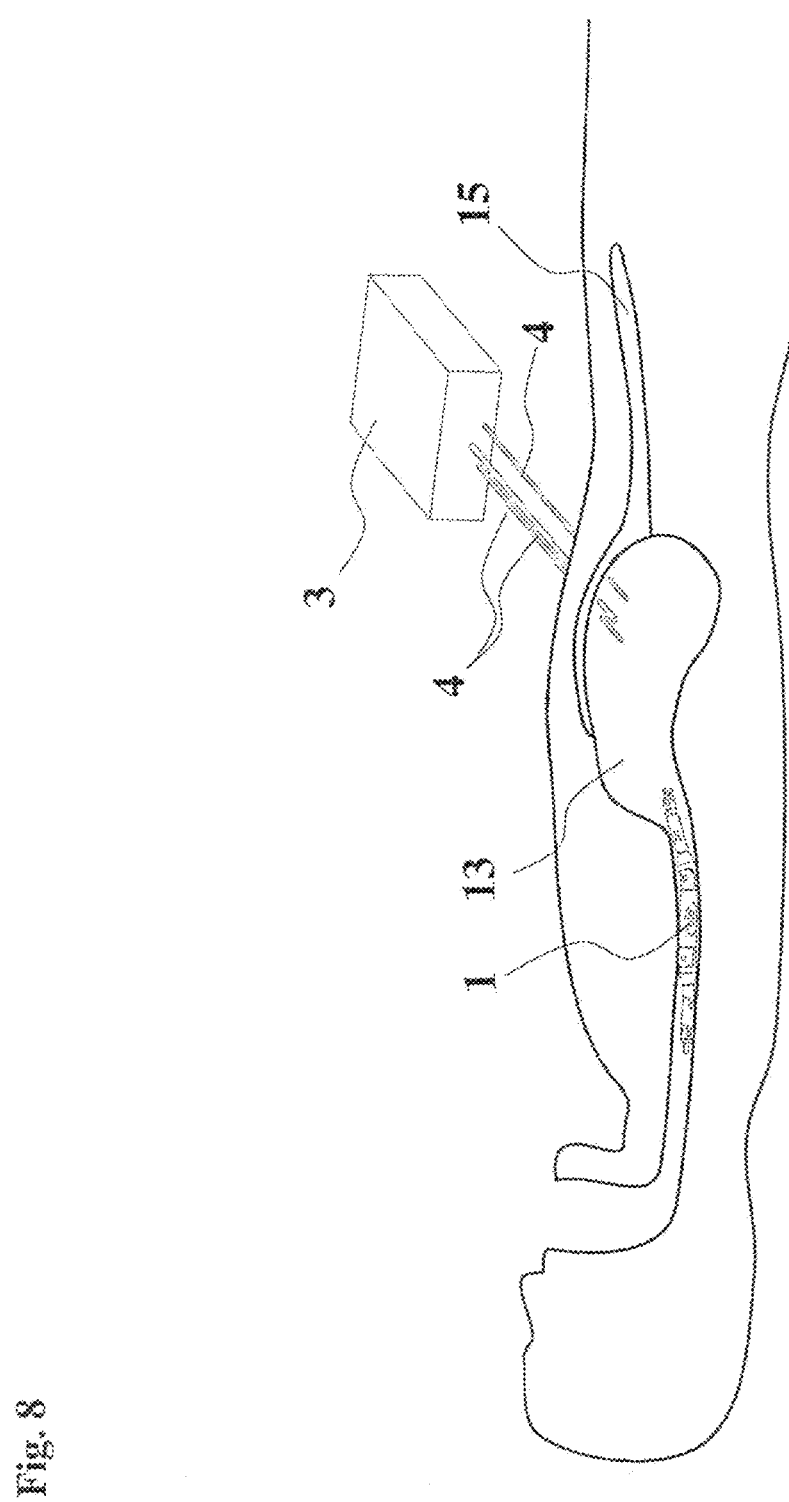
FIG. 8 is a view similar to FIG. 5 showing schematically an introduction of the intracorporeal unit into the patient's stomach.
Figure 9:
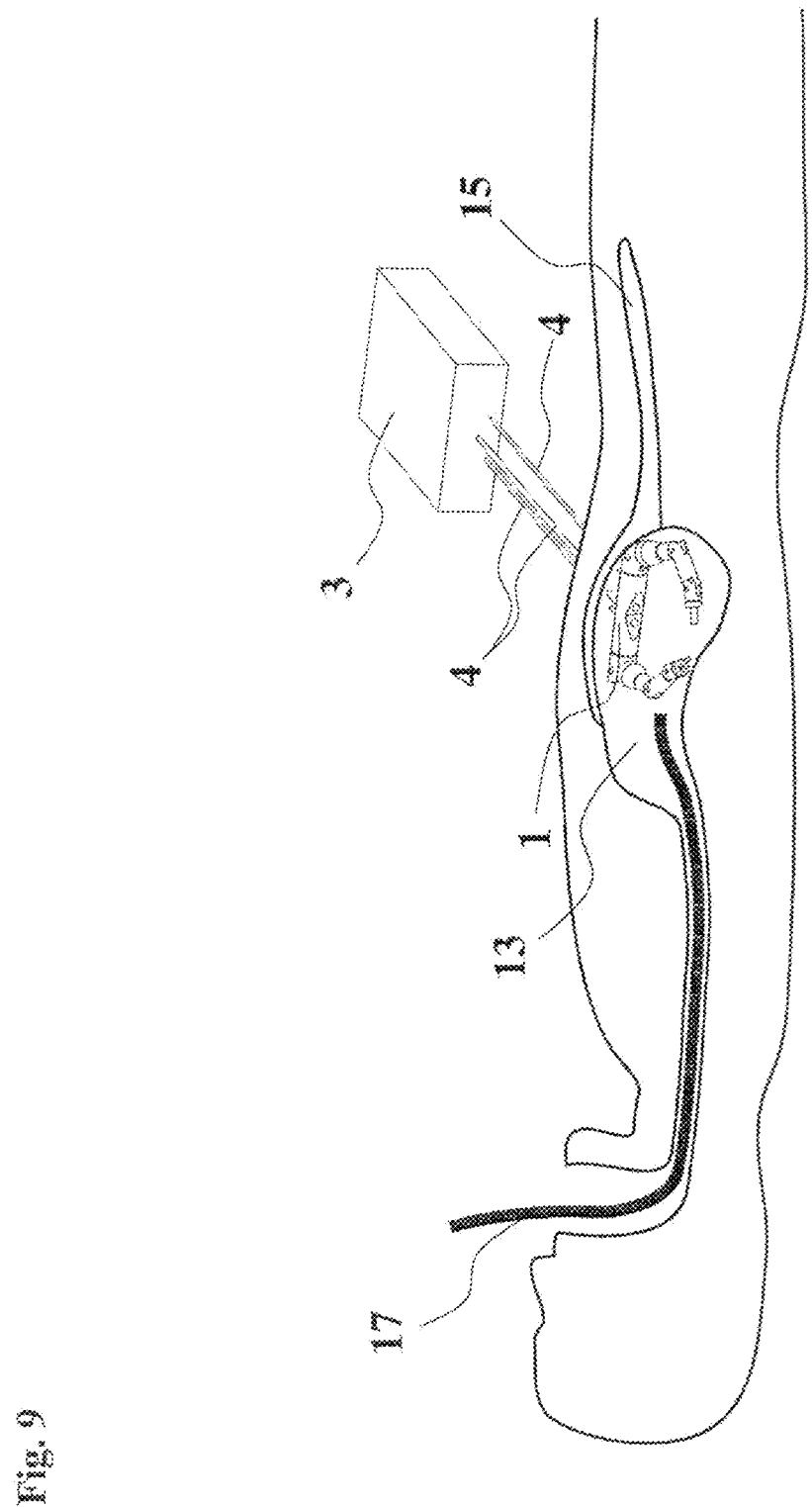
FIG. 9 is a view similar to FIG. 6, wherein a flexible endoscope is inserted through the esophagus into the stomach and wherein the intracorporeal unit is mounted to the connecting unit.
Figure 10:
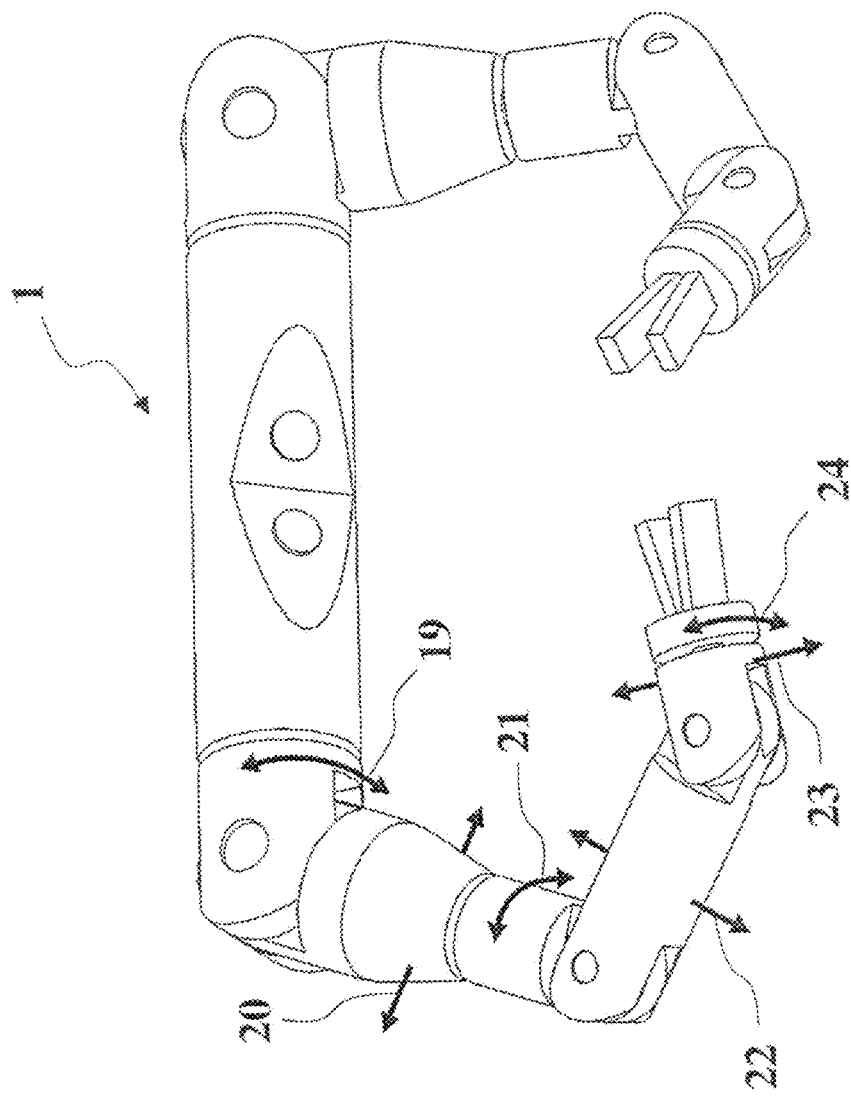
FIG. 10 is a view showing an intracorporeal unit and especially the degrees of freedom of the manipulator arm and/or surgical end effector according to the first embodiment of the surgical manipulator.
Figure 11:
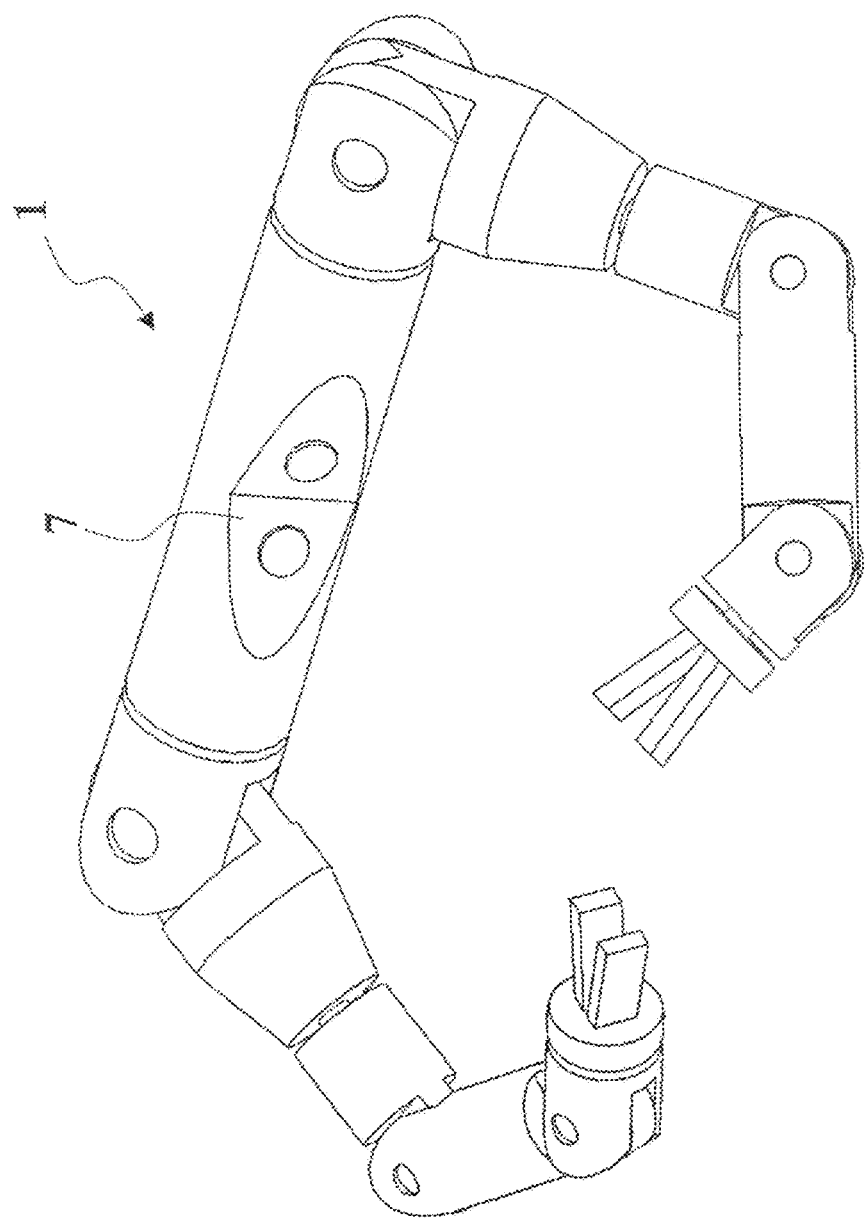
FIG. 11 is a view showing the intracorporeal unit of the surgical manipulator according to the first embodiment.

FIG. 1 shows a surgical manipulator comprising an intracorporeal unit 1, an extracorporeal unit 3 and a connecting unit 2. The intracorporeal unit according to the first embodiment is completely arrangeable within a body cavity 15 and has a central member 5 and two manipulator arms 6. The connecting unit 2 is for detachably mechanically connecting the intracorporeal unit 1 to the extracorporeal unit 3 when the intracorporeal unit 1 is arranged within the body cavity 15.

The connecting unit 2 is further adapted to being partly introduced into the body cavity 15 through at least two punctures in the body wall 16. Further, the connecting unit 2 is adapted to transmit control signals from the extracorporeal unit 3 to the intracorporeal unit 1.

In the first embodiment of the surgical manipulator, the connecting unit 2 comprises three connecting members 4 whose tip ends are to be pierced through the body wall 16 through separate punctures and are connectable to the intracorporeal unit 1. In detail, in the present embodiment, the connecting members 4 of the connecting unit 2 are connectable to the central member 5 of the intracorporeal unit 1. Further, no connecting member is connected to a manipulator arm of the intracorporeal unit 1. Additionally, the central connecting member 4 of the connecting unit 2 is adapted to transmit energy from the extracorporeal unit 3 to the intracorporeal unit 1, especially to the central member 5 of the intracorporeal unit 1.

In the following, the intracorporeal unit 1 is explained IN more detail. As already shown, the intracorporeal unit 1 according to the first embodiment of the surgical manipulator comprises two manipulator arms 6. Each of the manipulator arms 6 comprises a plurality of limbs and joints. As clearly can be seen from FIG. 10, the individual limbs have each a certain degree of freedom. That is, the joints of each manipulator arm 6 include swivel joints and torsion joints.

Figure 17:
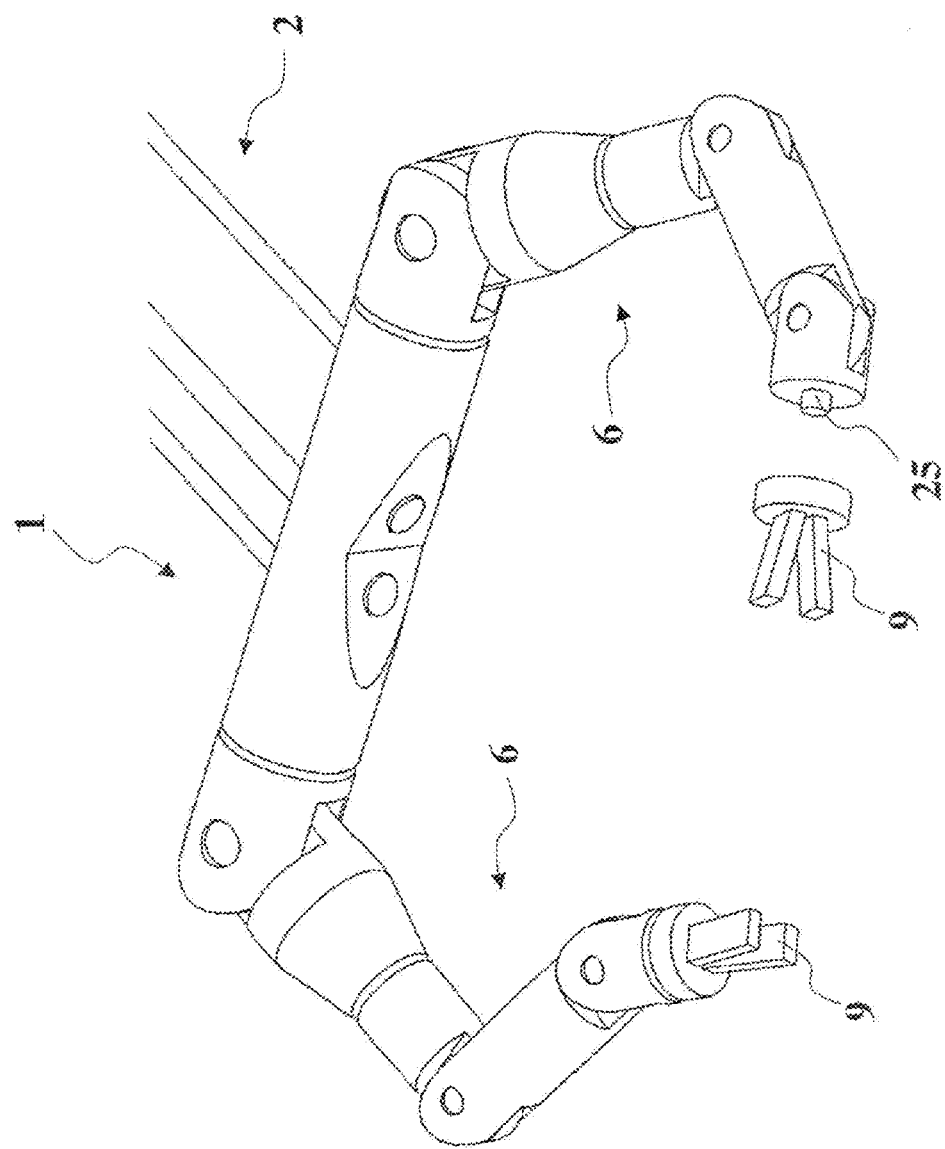
FIG. 17 is a view showing the intracorporeal unit according to the first embodiment of the surgical manipulator, wherein the surgical end effector is replaceably mounted to the manipulator arm.

Further, each manipulator arm 6 comprises a distal end a surgical end effector 9. In the present embodiment, the surgical end effector 9 is a simple rasping device, wherein any known kind of other surgical end effector 9 may also be provided to one or both manipulator arms 6. As it is shown in FIG. 17, the surgical end effector 9 is mounted to the distal end 25 of the concerned manipulator arm 6, is replaceable and exchangeable.

As it has already been described above, and as it is shown in FIG. 10, the surgical end effectors 9 being movable relative to the central member 5 with plural degrees of freedom 19 to 24. In the present embodiment, the degrees of freedom of the surgical end effector relative to the central member 5 of the intracorporeal unit are substantially identical to the degrees of freedom a human hand relative to the shoulder. In other words, the character and number of the degrees of freedom of each manipulator arm 6 is substantially identical to a human arm. That is, the surgical end effector 9 can move approximately in the same way as a human hand can.

Further, the central member 5 of the intracorporeal unit 1 comprises a monitor 7 monitoring the sphere of action of the two manipulator arms 6. In the present embodiment, the monitor 7 is a stereoscopic camera 7 able to three-dimensionally monitor the sphere of action of the manipulator arms 6. Moreover, the central member 5 of the intracorporeal unit 1 comprises an illuminator 8 for illuminating the sphere of action of the manipulator arms 6. In the present embodiment, the illuminator 8 is merely provided to the central member 5 of the intracorporeal unit 1. Alternatively or additionally, an illuminator may also be provided to one or more of the limbs of the manipulator arms 6.

The intracorporeal unit 1 is introduced into the patient's body through a natural body orifice, e.g. an esophagus. Therefore, the intracorporeal unit 1 may have a diameter of approximately 20 mm.

Figure 18:
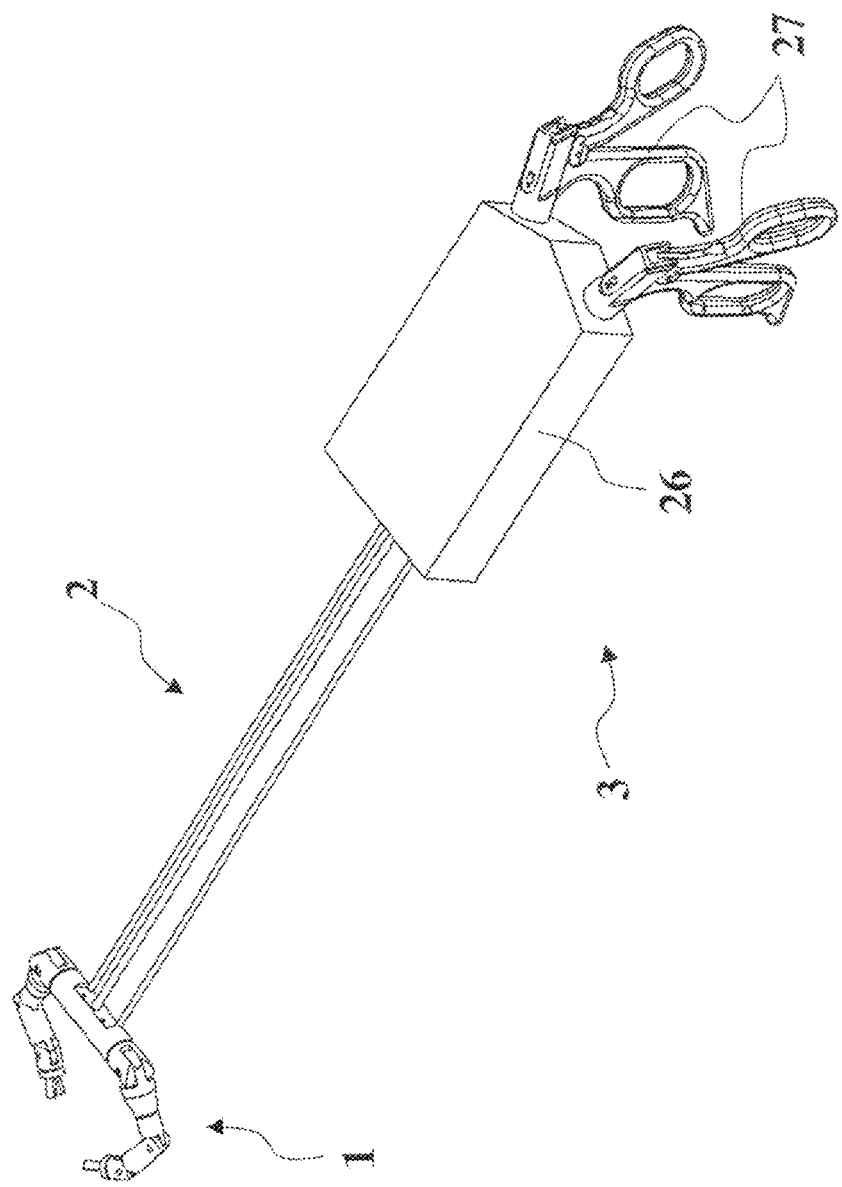
FIG. 18 is a view showing the surgical manipulator according to the first embodiment.

Referring to FIG. 18, the extracorporeal unit 3 of the surgical manipulator according to the first embodiment is described in more detail. The extracorporeal unit 3 comprises two handles 27 via which the two manipulator arms 6 and the corresponding surgical end effectors 9 are controllable. As it has been described above, the degrees of freedom of the intracorporeal unit 1 according to the first embodiment correspond to the degrees of freedom of a human hand. The manual handles 27 of the extracorporeal unit 3 are in the form of a grip of a scissors. That is, by actuating a manual handle 27, the corresponding surgical end effector 9 is opened or closed. The manual handles 27 are attached to an electromechanical linkage 26 in such a way that the operator can grip both manual handles 27 ergonomically. The electro-mechanical linkage 26 is for transforming the movements of the manual handles 27 into mechanical signals transmitted through the connecting members 4 of the connecting unit 2 to the intracorporeal unit 1. Further, the electro-mechanical linkage 26 also sends electricity to the intracorporeal unit 1 for illumination and receives signals of the stereoscopic camera and outputs these signals to a monitor or display not shown in the Figs. The manual handles may have different shapes, as they are known for manual handles in the state of the art.

Figure 22:
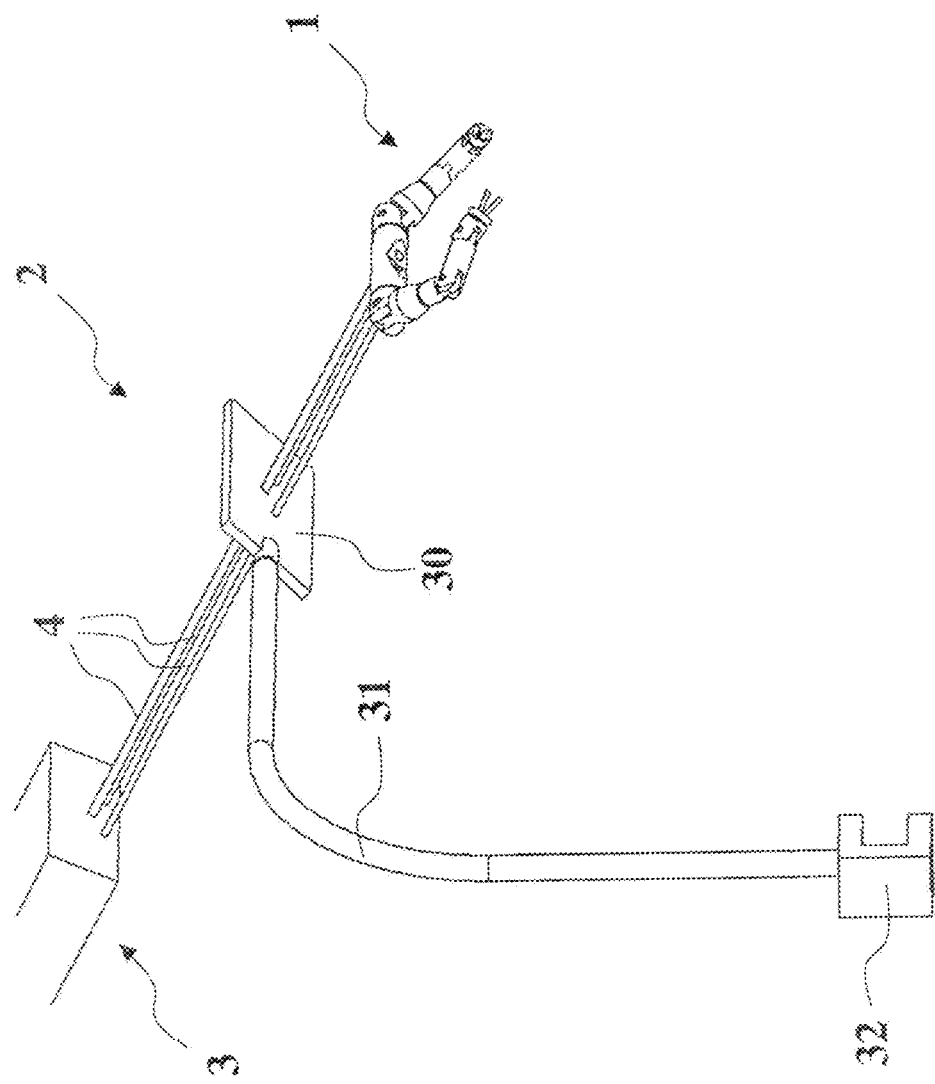
FIG. 22 is a view showing a surgical manipulator according to the first embodiment, wherein the connecting unit is held by a bearing device.
Figure 23:
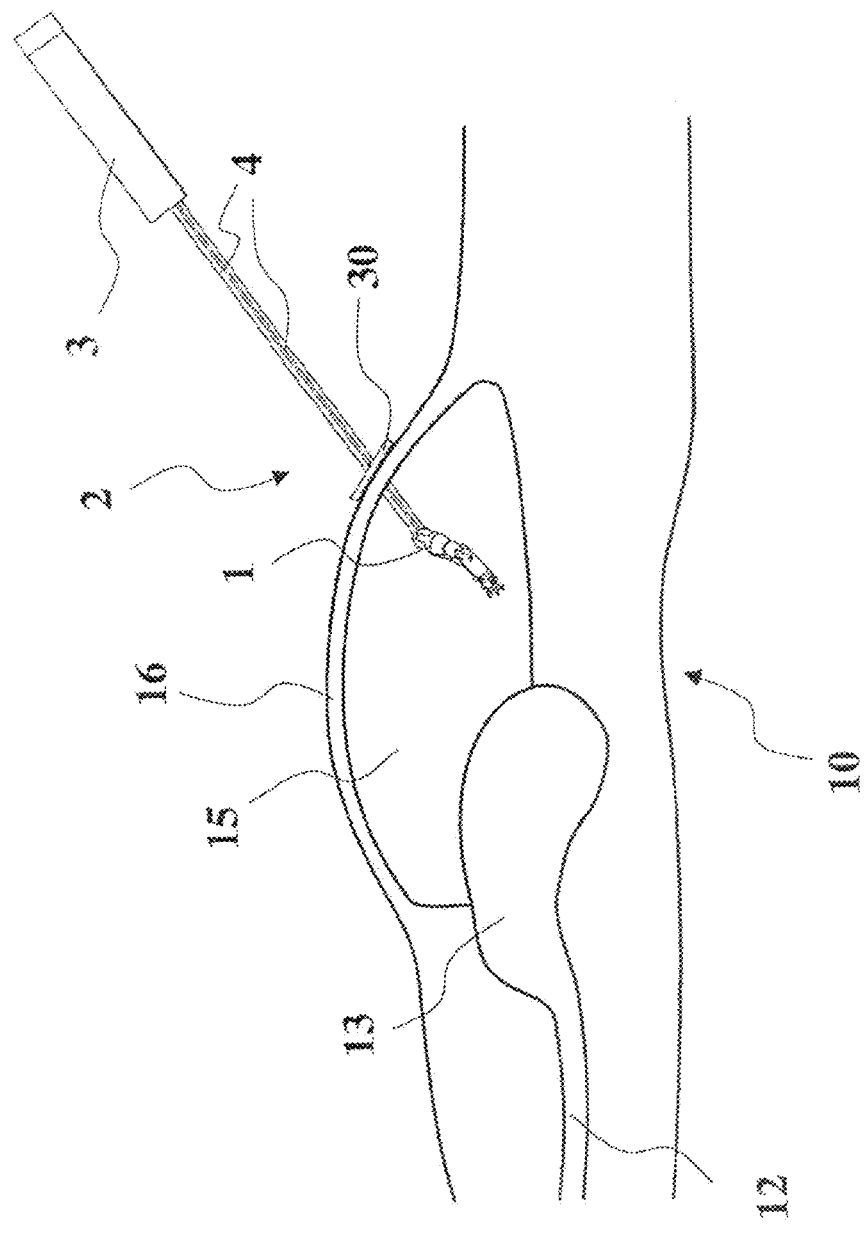
FIG. 23 is a schematic view showing a longitudinal section through a patient's body, wherein a surgical manipulator according to the first embodiment and a bearing device are used for operation within the abdomen of the patient.

Further, in FIG. 22, a bearing device 30 is shown which bears the connecting unit 2 in such a way that the connecting unit 2 is able to be rotated and actually shifted relative to the bearing device 30. The position of the bearing device 30 relatively to the concerned body cavity 16 is adjustable via a holding arm 31 which has flexibility and is fixable relative to the patient via a fixing means 32. That is, the bearing device 30 most preferable abuts to the outside of the abdomen wall 16 of the patient. Then, the risk of injuring of the abdomen wall 16 of the patient during operation is minimized since the bearing device 30 does not allow a transversal movement of the connecting members 4, that is, a movement in a plane of the abdomen wall 16.

Figure 12:
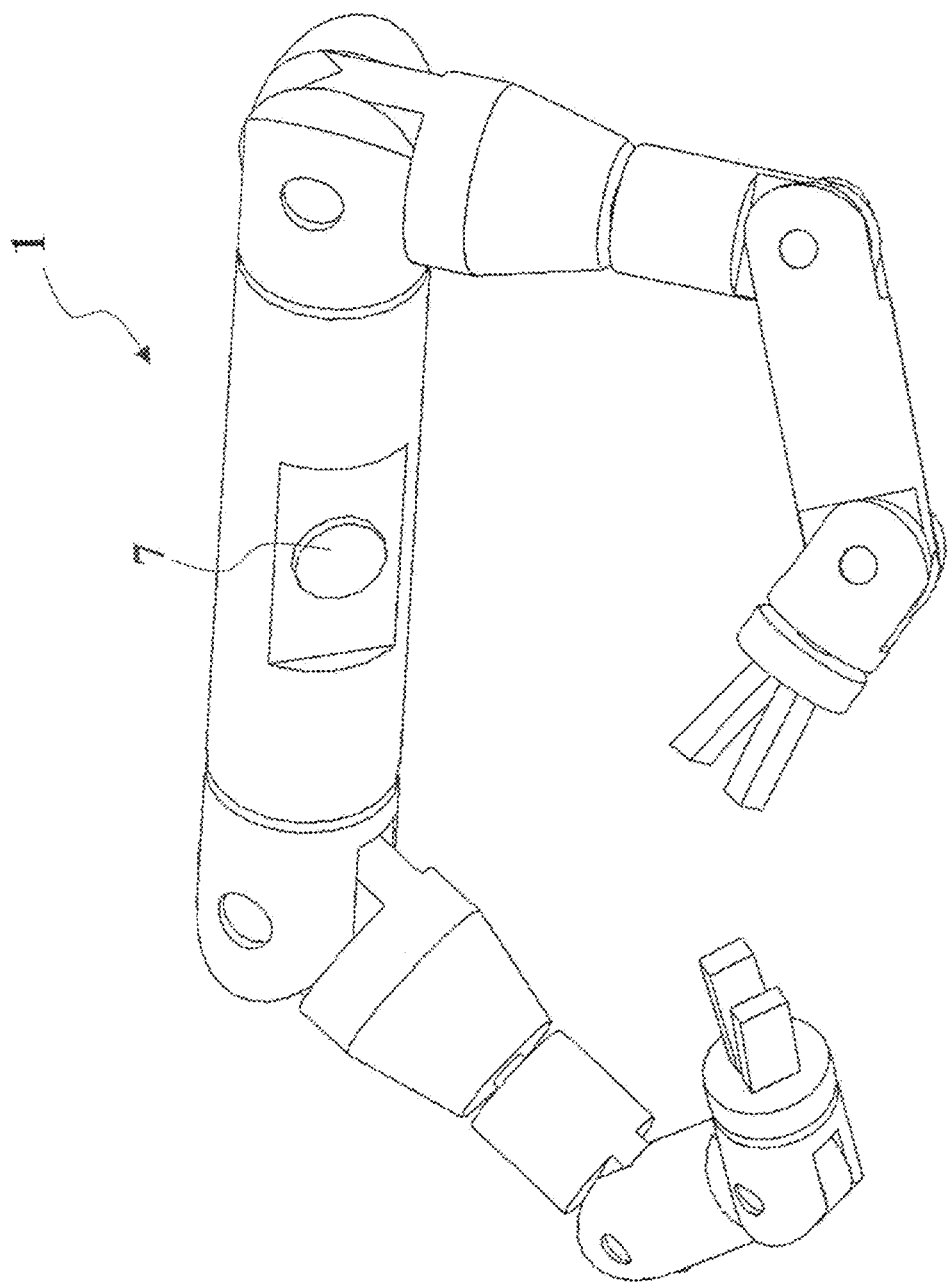
FIG. 12 is a view showing an intracorporeal unit according to a second embodiment of the surgical manipulator.

In the following, a second embodiment of the surgical manipulator is described by reference to FIG. 12. The second embodiment of the invention differs from the first embodiment only in the monitor 7 and in that no illuminator 8 is provided to the surgical manipulator. That is, illumination is effected separately from the surgical manipulator of the present embodiment. While in the first embodiment a stereoscopic camera is provided which is able to monitor the sphere of action of the manipulator arms 6 three-dimensionally, in the second embodiment a normal video camera is provided. Under normal circumstances, a three-dimensionally monitoring stereoscopic camera is not inevitably required and a normal video camera may be sufficient for the operator to monitor the sphere of action of the manipulator arms 6. Of course, an illuminator as in the first embodiment may also be provided in the second embodiment, either instead or additional to a separate illuminator.

Figure 13:
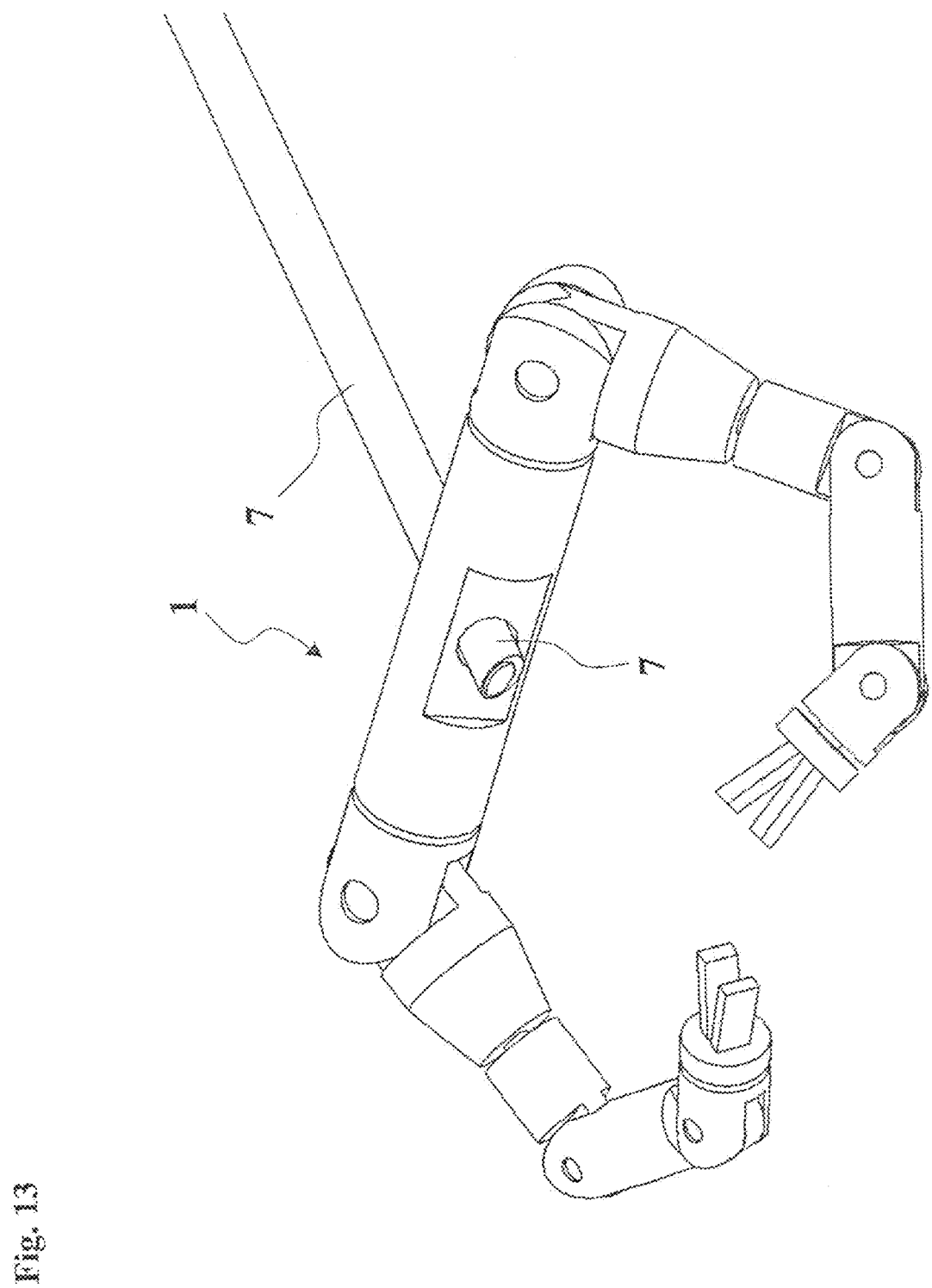
FIG. 13 is a view showing an intracorporeal unit according to a third embodiment of the surgical manipulator.

In the following, a third embodiment of the present invention is described by reference to FIG. 13. In the third embodiment of the surgical manipulator, no stereoscopic camera or video camera is provided to the intracorporeal unit 1 at all but a video camera 7 is provided separately from the intracorporeal unit 1. The central member 5 of the intracorporeal unit 1 is provided with a through-hole through which a video camera 7 can be passed such that the location and orientation of the video camera 7 relative to the central member 5 of the intracorporeal unit 1 is determined.

In such a case, the video camera 7 may be either provided to one of the connecting members 4 of the connecting unit 2 or may be provided to a separate member which is provided only for holding the video camera 7. In FIG. 13, a case is shown, where the video camera 7 is not provided at a tip end of a connecting member 4 but wherein the video camera 7 is provided to a tip end of a separate member. Further, in FIG. 13, no connecting members 4 of the connecting unit 2 are shown at all. For maintaining the set location of the video camera 7 relative to the intracorporeal unit 1, the video camera may be fixed relative to the central member 5 of the intracorporeal unit 1 either by direct connection between the separate member and the central member 5 or by fixing e.g. the separate member to the extracorporeal unit 3. In the third embodiment, the connecting unit 2 of the surgical manipulator consists of two connecting members 4. Of course, each camera system 7 according to any embodiment may also be configured pivotally to be able to center on any location of interest.

Further, an illuminator may either be provided to the separate member holding the video camera 7 or to the central member 5 or any limb of any manipulator arm 6 of the intracorporeal unit 1.

Next, a fourth embodiment of the surgical manipulator is explained by reference to FIGS. 14 and 21.

Figure 14:
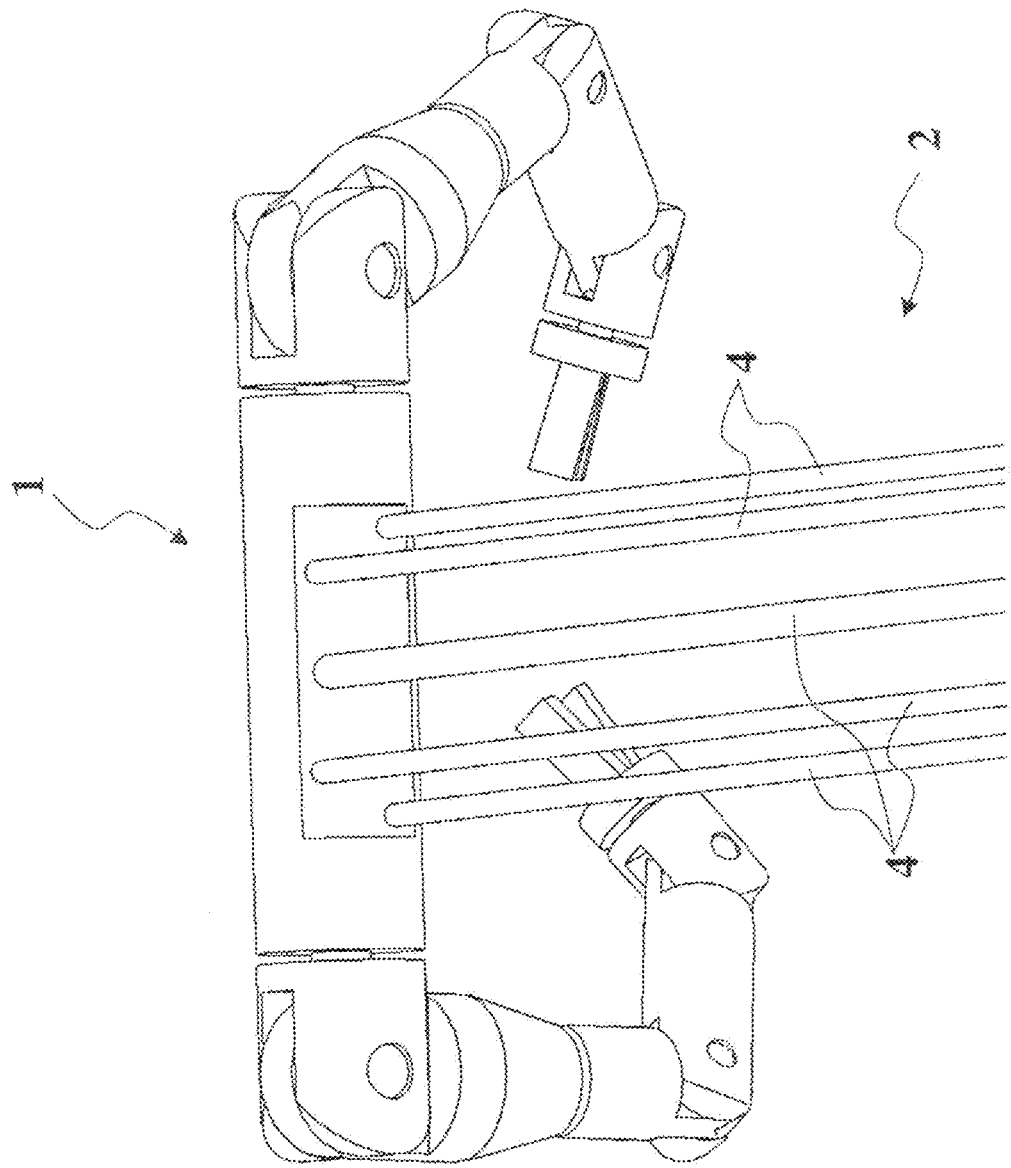
FIG. 14 is a view showing an intracorporeal unit and a connecting unit according to a fourth embodiment of the surgical manipulator.
Figure 15:
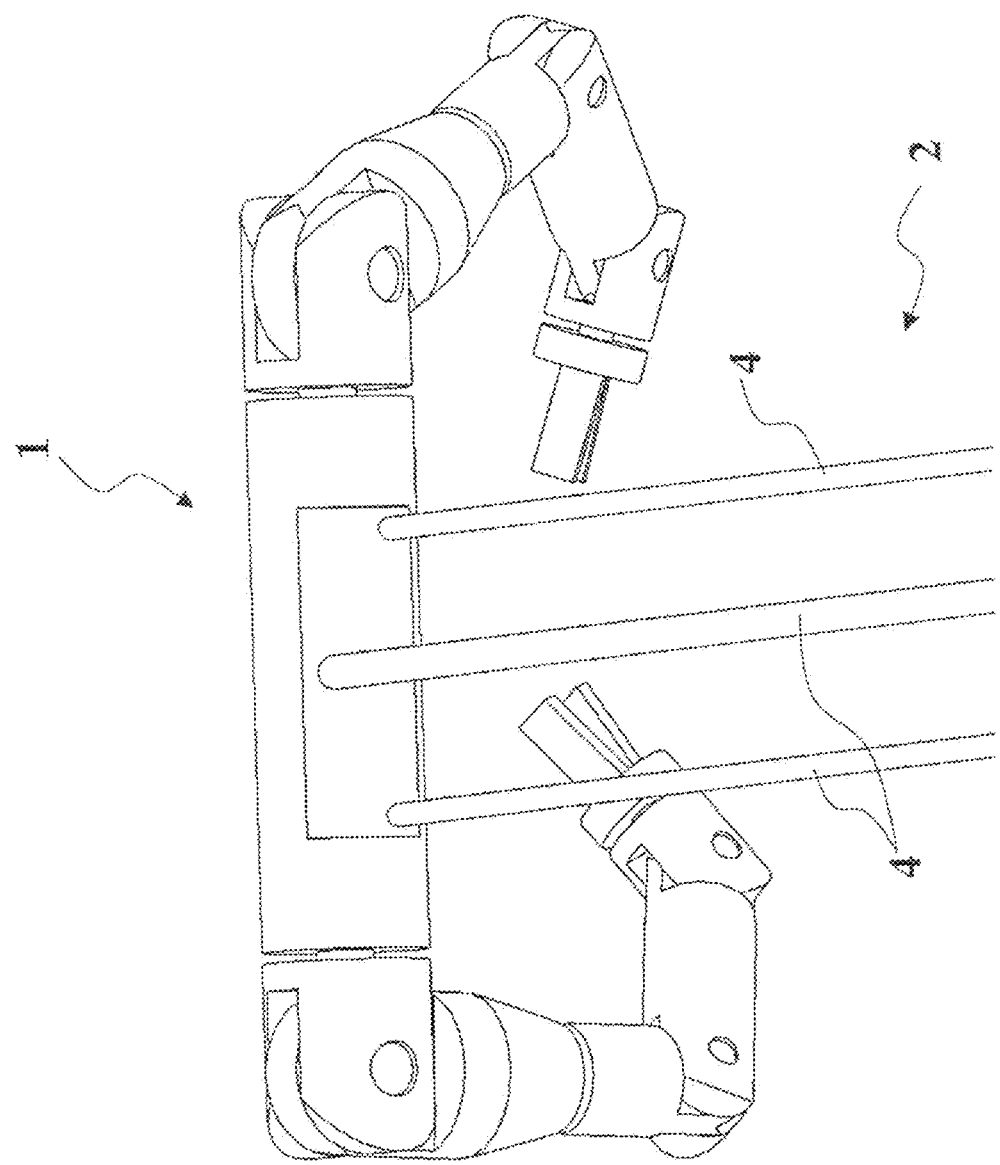
FIG. 15 is a view showing the intracorporeal unit and the connecting unit according to the first embodiment of the surgical manipulator.

As can be seen from FIG. 14, in the fourth embodiment of the surgical manipulator, the central member 5 of the intracorporeal unit 1 is connected to the extracorporeal unit 3 by means of five connecting members 4. That is, the connecting unit 2 according to the fourth embodiment consists of five connecting members 4. In this case, the diameter of each connecting member 4 may be further minimized such that the incisions made for introducing the tip ends of the connecting members 4 into the patient's body may be further minimized so that wound healing of the incisions is further promoted. Additionally, in case more connecting members 4 are provided, the signals concerned with the respective limb of the respective manipulator arm 6 may be separated from each other so that possible interferences are avoided.

For example, the signals for opening and closing the grasping device, which is the surgical end effector 9 in the present embodiment, may be electric signals and may be transferred from the extracorporeal unit 3 to the intracorporeal unit 1 via a specific connecting member 4 (e.g. upper left connecting member for left manipulator arm 6 in FIG. 14). Then, the signals for moving the limbs of the respective manipulator arm 6 may be mechanical signals, e.g. fluidic signals, which are transmitted from the extracorporeal unit 3 to the intracorporeal unit 1 via another connecting member 4 (e.g. lower left connecting member for left manipulator arm 6 in FIG. 14). That is, in the present case, electric signals are transmitted separate from mechanical signals. Further, the central connecting member may be provided for transmitting video signals from the intracorporeal unit 1 to the extracorporeal unit 3 and for transmitting electricity for an illuminator (not shown) in the opposite direction.

A further advantage of the provision of a higher number of connecting members 4 is that mechanical forces acting onto the intracorporeal unit 1 during operation may be further divided and more easily absorbed.

Figure 21:
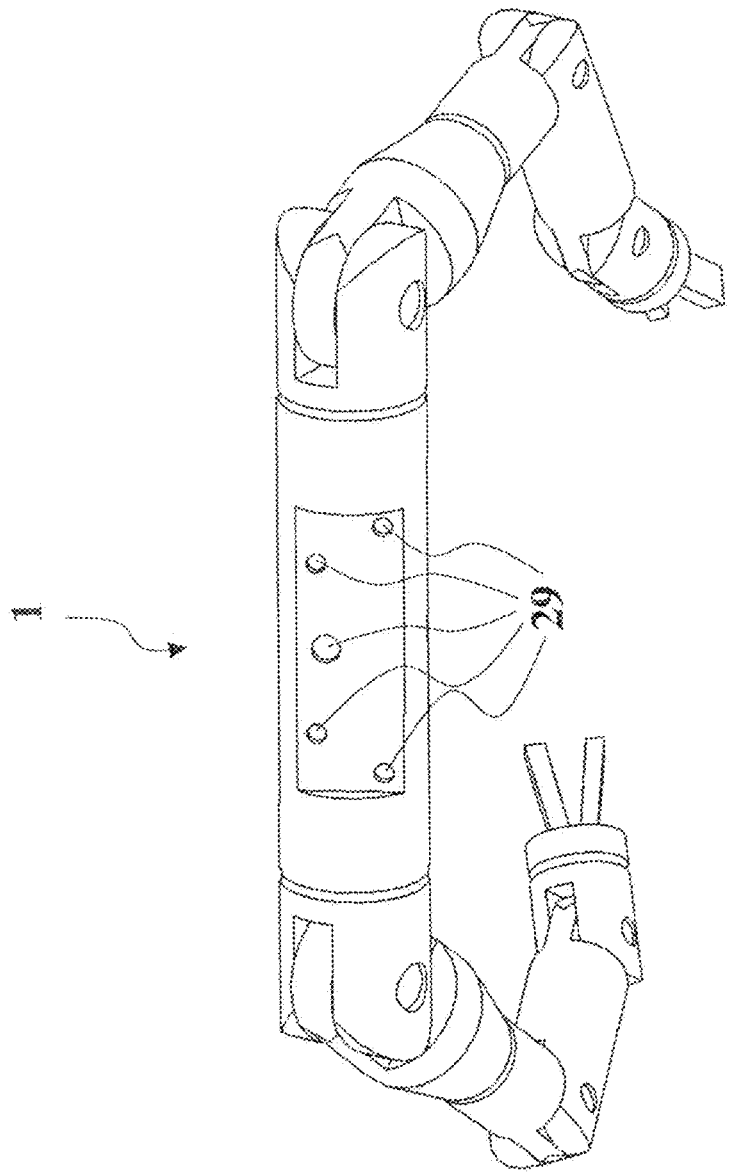
FIG. 21 is a view showing the intracorporeal unit according to the fourth embodiment from backside.

In FIG. 21, a backside of the intracorporeal unit 1 is shown, wherein the central member 5 has a mounting plate comprising five sockets 29 for receiving the tip ends of the respective connecting member 4. The sockets 29 and the tip ends of the connecting members 4 are configured to transmit mechanical and/or electrical signals.

Figure 26:
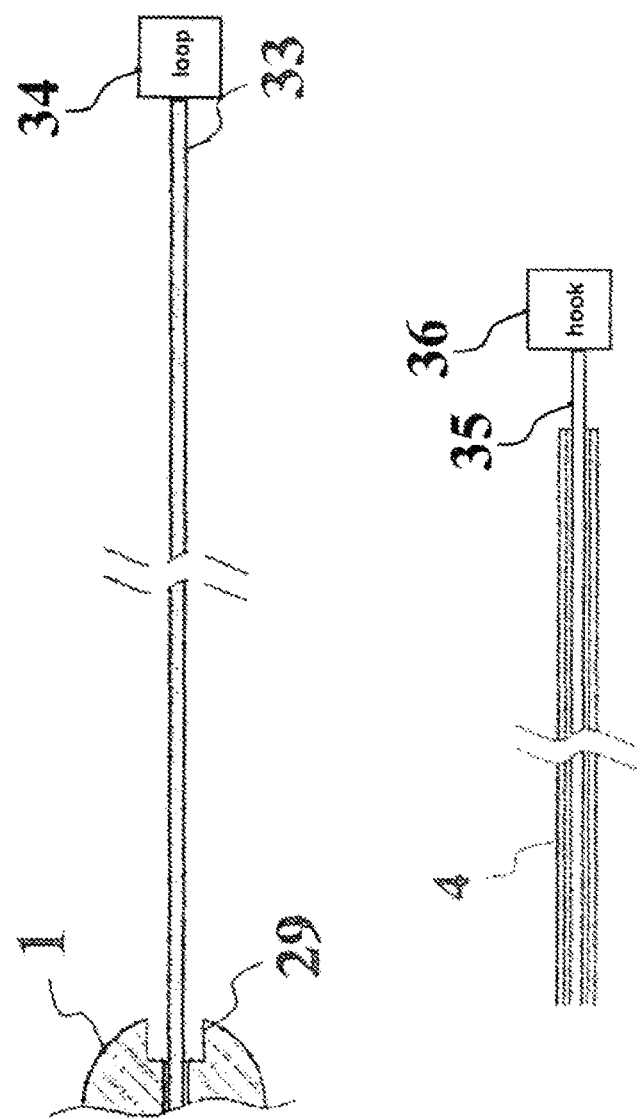
FIG. 26 shows an example connection between the intracorporeal unit and the connecting unit.

In the following, one example of making connection between the intracorporeal unit 1 and the connecting unit 2 is explained. With reference to FIG. 26, at least one socket 29 is provided with a tension wire 33 attached to the respective socket 29 at one end and comprising a loop 34 at its opposite end. Further, the connector 4 of the connecting unit 2 corresponding to the socket 29 with tension wire 33 has an axial groove or preferably an axial through hole. Through the axial through hole a catch wire 35 is passed having at its tip end some kind of hook 36 for catching the loop 34 of the tension wire 33 of the socket 29. When the connecting unit 4 has been introduced into the patient's body, the surgeon catches loop 34 of the tension wire 33 with the hook 36 of the catching wire 35. Since at that time the intracorporeal unit 1 is not yet energized (no energy and signal transfer between connecting unit 2 and intracorporeal unit 1 is possible before docking) the surgeon preferably uses an endoscopic camera for this process. The endoscopic camera may be introduced into the patient's body on the same way as the intracorporeal unit. Then, the surgeon pulls back the catching wire 33 so that the tension wire 33 is pulled into the through hole of the respective connecting member 4. When the tip end of the connecting member 4 has docked at the socket 29 of the intracorporeal unit 1, the surgeon fixes the tension wire 33 to maintain the docked state. Usually, more than one connecting member 4 and more than one socket 29 get connected in this way so that an adequate firm and rigid connection between intracorporeal unit 1 and connecting unit 2 is secured.

After operation, the surgeon releases the tension wire(s) 33 in order to separate the intracorporeal unit 1 from the connecting unit 2. In case of an emergency or in case release of the tension wire(s) 33 is not possible due to damage, the surgeon may also cut the tension wire(s) 33. This is possible since the tension wire(s) 33 are passed through the incisions in the body wall to outside the patient's body.

Figure 16:
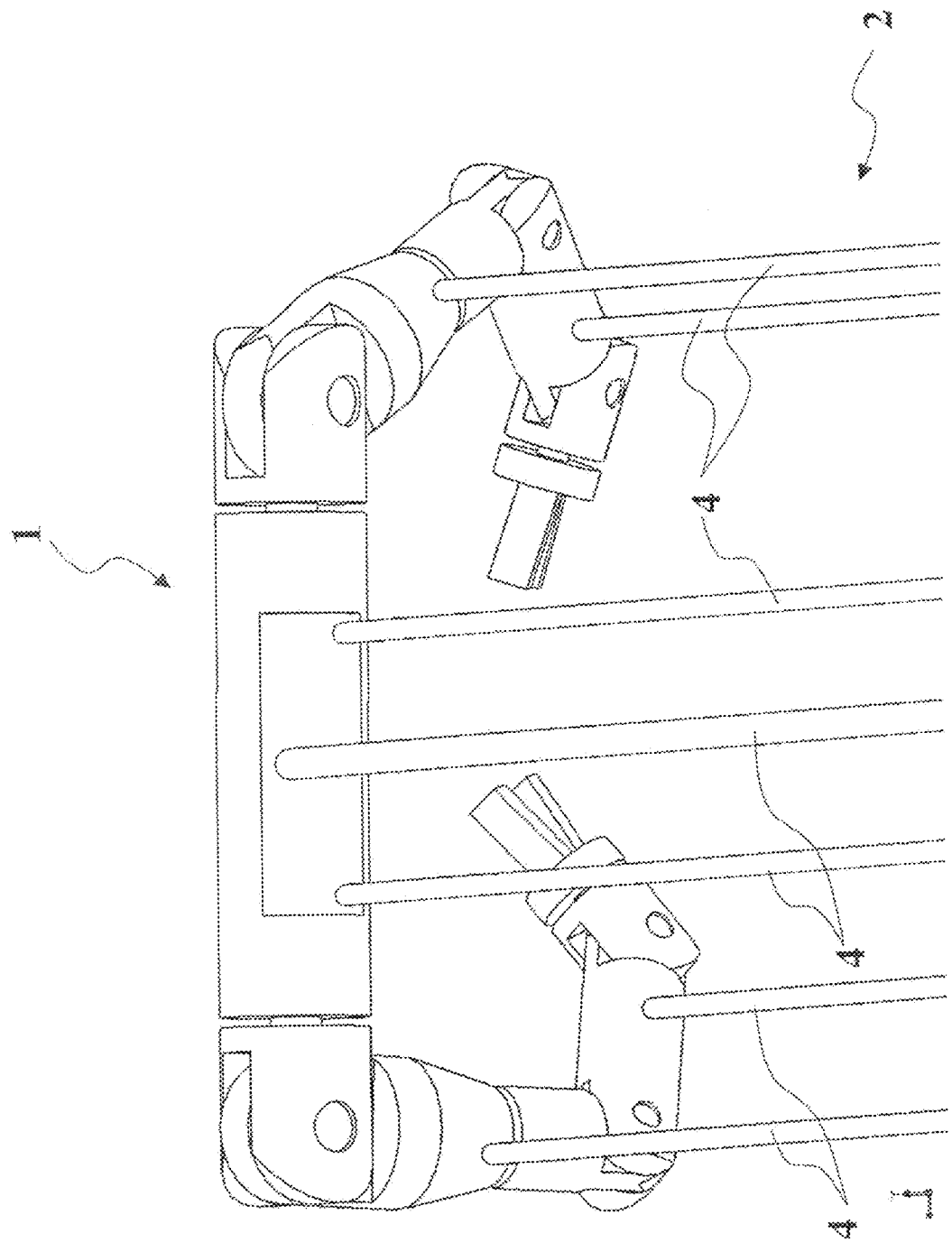
FIG. 16 is a view showing an intracorporeal unit and a connecting unit according to a fifth embodiment of the surgical manipulator.

Next, under reference to FIG. 16, a fifth embodiment of the surgical manipulator is explained. In the fifth embodiment, not only the central member 5 of the intracorporeal unit 1 is connected to the extracorporeal unit 3 by connecting members 4, but also some of the limbs of the manipulator arms 6 are connected to the extracorporeal unit 3 by connecting members 4. That is, the connecting unit 2 consists of a plurality of connecting members 4 which are connected to the central member 5 as well as to the manipulator arms 6 of the intracorporeal unit 1.

As it is shown in FIG. 16, two connecting members 4 are connected to two limbs of each manipulator arm 6, respectively. By moving the connecting members 4, which are connected to the limbs of the manipulator arms 6, the manipulator arms 6 can be moved directly without the need of transmitting signals through these connecting members 4. However, additionally to moving the connecting members 4 and moving the respective limbs of the manipulator arms 6 directly, the connecting members 4 connected to the limbs may also transmit for example electric signals for the adjacent limbs or may transmit energy to the limb for an illuminator provided to this limb.

Figure 19:
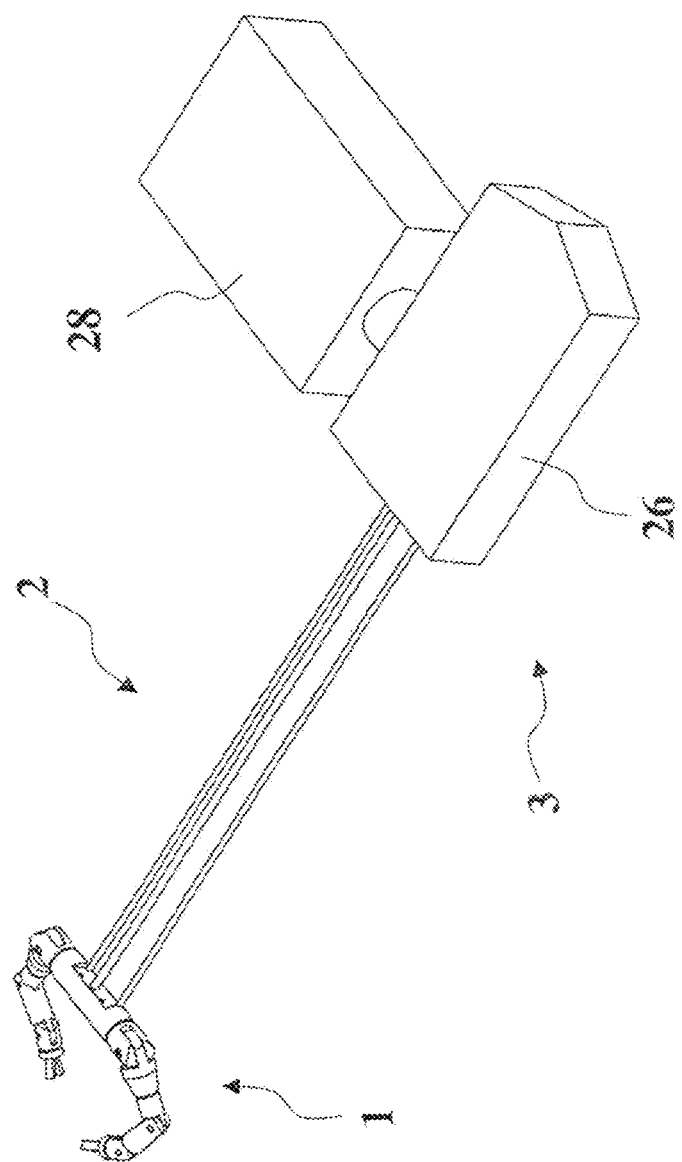
FIG. 19 is a view showing a sixth embodiment of the surgical manipulator.

In the following, a sixth embodiment of the surgical manipulator is explained under reference to FIG. 19. As can be seen from FIG. 19, no manual handles 27 are provided to the extracorporeal unit 3 but an actuator 28 is provided to the transmitter 6 of the extracorporeal unit 3 instead of the manual handles 27. The actuator 28 may be controlled by a computer system or may be remote controlled via the internet or other networks and provide the actuations for the manipulator arms 6 and the surgical end effectors 9 of the intracorporeal unit 1.

By remote control of the surgical manipulator via e.g. the internet, a specialized surgeon may carry out an operation without being on site.

The actuator 28 may either receive control signals in real time from any kind of known input device or may have a memory device in which a certain operation program has been previously stored.

Figure 20:
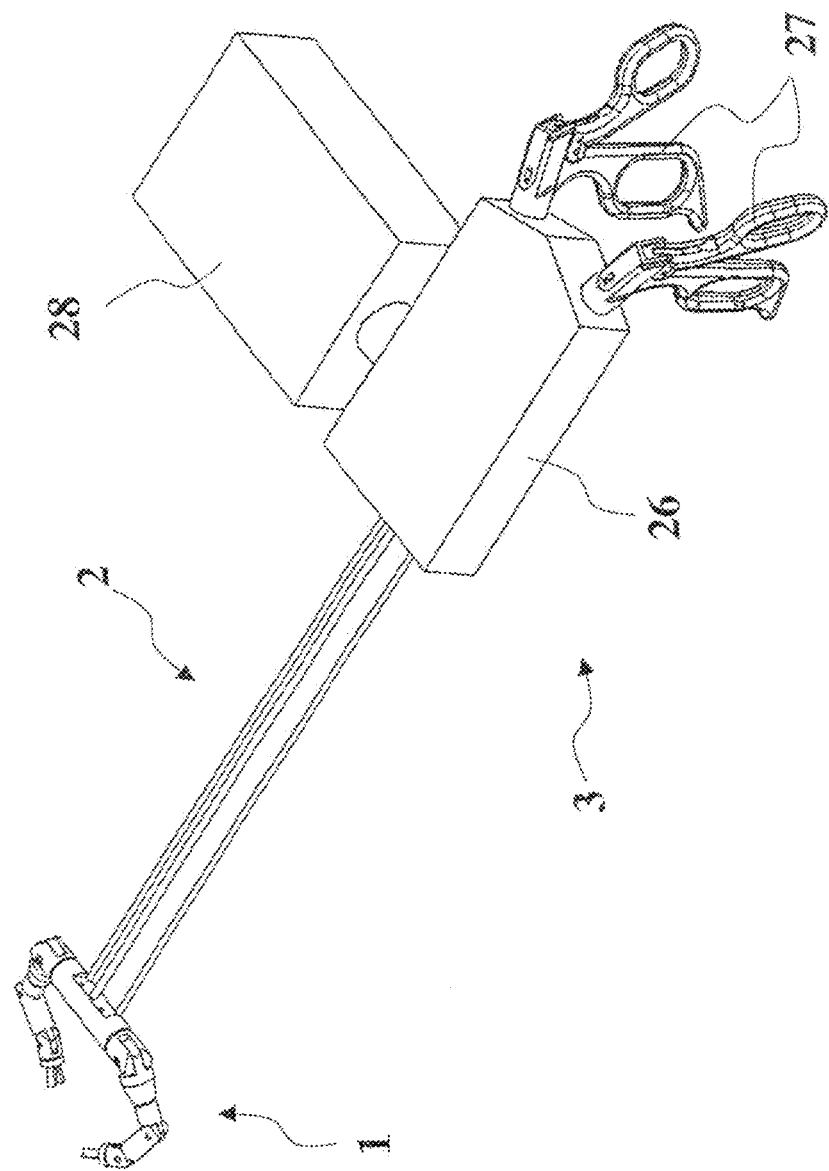
FIG. 20 is a view showing a seventh embodiment of the surgical manipulator.

Now, a seventh embodiment of the surgical manipulator is explained under reference to FIG. 20. In FIG. 20, an intracorporeal unit 3 is shown which comprises manual handles 27 as well as an actuator 28. That is, the surgical manipulator according to the seventh embodiment may be either controlled by manual handles 27 and actuator 28 successively or simultaneously.

For example, the manual handles 27 may only be used for opening and closing the surgical end effectors 9 and the actuator 28 may control the movements of the limbs of the manipulator arms 6. In such a case, an operator may concentrate on gripping and handling e.g. the patient's body tissue. The signals of the actuator 28 may be either electric or mechanical signals. The signals transmitted from the transmitter 26 to the intracorporeal unit 1 may also be electrical signals and/or mechanical signals.

In the seventh embodiment, as well as in the other embodiments too, the transmitter 26 may also include a means for monitoring the inputs of the input devices such as manual handles 27 and actuator 28. In case an input from any of these input means may bear the danger of injuring the patient, the transmitter 26 either stops movement of the manipulator arms 6 immediately or modifies the input in such a way that injury of the patient is surely avoided. That is, extreme fast or powerful movements are attenuated in order to prevent the patient and his body from damage.

Further, plural modifications and combinations of the above embodiments of the surgical manipulator are contemplated. Specifically, different configurations of the intracorporeal unit 1 may be combined with different configurations of the extracorporeal unit 3.

For example, more than two manipulator arms 6 may be provided to the intracorporeal unit 1 or more than one manual handle 27 may be provided for each manipulator arm. Further, instead of manual handles 27, other input devices may be provided to the extracorporeal unit 3. Additionally, optical signals may be transferred from the extracorporeal unit 3 to the intracorporeal unit 1 or in the opposite direction via the connecting unit 2.

In another modification of the above embodiments, the control signals may be wirelessly transmitted from the extracorporeal unit to the intracorporeal unit 1 and only energy is transmitted from the extracorporeal unit 3 to the intracorporeal unit 1 via the connecting unit 2. It is further contemplated to transmit energy wirelessly from outside the patient's body to the intracorporeal unit. When applying this technique it has to be considered that heat generation within the patient's body does not harm the patient.

Further, some kind of magazine may be provided to the intracorporeal unit 1, e.g. to the central member 5, such that during introduction of the intracorporeal unit 1 into the patient's body, the surgical end effectors 9, which may injure the patient during introduction of the intracorporeal unit 1, may be received within the magazine, such that the patient's body is prevented from injury during introduction of the intracorporeal unit 1. Further, such a magazine may contain more than one surgical end effector 9 per manipulator arm 6 such that the operator may exchange the surgical end effector 9 mounted to a specific manipulator arm 6 during operation within the patient's body. For example, the operator may exchange a grasping device for a cutting device or something else. Additionally or alternatively, a separate magazine may be introduced into the patient's body. In order to preserve the body orifice via which the intracorporeal unit 1 and the separate magazine are introduced into the patient's body, a protection tube may be introduced first through which the other means and devices are introduced.

Moreover, various input devices are contemplated instead of or additionally to the manual handles 27 and the actuator 28. For example, some kind of joystick may be provided for controlling the movement of the manipulator arms 6.

The intracorporeal unit 1 may also be provided with pressure sensors. Specifically, surgical end effectors 9 in the form of grasping devices may be provided with pressure sensors. Then, the control devices, as for example the manual handles 27, may be provided with force-feedback means for giving the surgeon mechanical/tactile feedback. This feedback operates to make the operation of the surgical manipulator more intuitive.

Instead of manual handles 27, the extracorporeal unit 3 may also comprise another kind of control means. For example, the surgeon may hold a locating device in his/her hand whose position and attitude can be three-dimensionally captured by a capturing device. The capturing device monitors the movements of the locating device and computes the movements of the manipulator arms 6 in such a way that the concerned surgical end effector 9 moves similar to the locating device. Thereby, the movements of the surgical end effector 9 may be appropriately downscaled.

The movements of the surgeon's arms and hands may also be detected by some sort of glove which is able to detect the movements of each pair of adjacent limbs of the surgeon's arm. It is also possible to provide sensors (not shown in the figures) at/in the intracorporeal unit which detect movements or forces applied to the joints/effectors of the intracorporeal unit 1. The detector signals can then be transferred into a respective adjustment of the manual control elements (handles, joy sticks etc) to create a haptic feedback.

Figure 24:
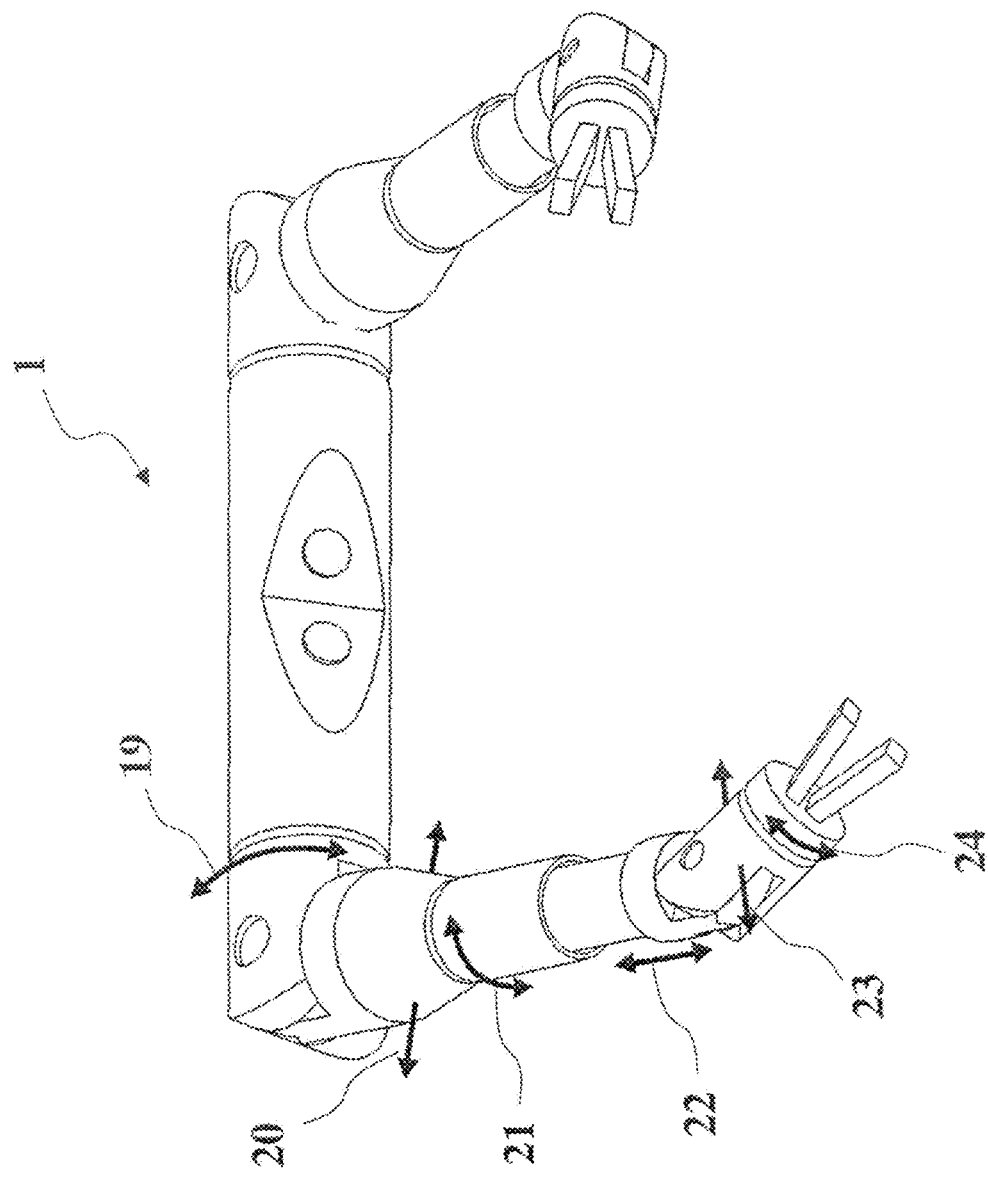
FIG. 24 is a schematic view of an intracorporeal unit according to an alternative design.

In FIG. 24 an alternative embodiment of the invention is shown. Here, the manipulator arms have telescope portions which can be reciprocally extended/retracted. Such a translatory movement can be effected by electric, hydraulic or pneumatic actuators supplied with energy via the connecting unit especially via the plurality of shafts 4.

In FIGS. 25a to 25g a plurality of different plug/socket designs are shown.

According to FIG. 25a the connecting element (or shaft) 4 is connected with the intracorporeal unit 1 (central portion) in a rigid manner.

In FIG. 25b the connecting element (or shaft) 4 connected with the intracorporeal unit 1 in a rigid manner has an internal channel or conduit extended axially of the shaft.

FIG. 25c shows a rigid interconnection between the intracorporeal unit 1 and the connecting element (shaft) 4 wherein in this design a cable 33 is accommodated within the conduit already shown in FIG. 25b. This cable 33 is (detachably) connected with the intracorporeal unit 1 and represents a possible design for the inventive guide. In other words, in case the intracorporeal unit 1 and the distal ends of the shafts 4 have to be coupled with each other, the cable 33 within each shaft or within only selected shafts will be extended or moved out and will be interconnected with the intracorporeal unit 1. Thereafter, the cable(s) 33 are pulled back until the distal ends of the shafts 4 are plugged in the respective sockets 29 at the intracorporeal unit 1.

According to FIG. 25d the connecting element (shaft) 4 is pivotally connected to the intracorporeal unit 1. Here, the socket 29 has a concave shape wherein the cable 33 extending axially within the conduit of the shaft is connected at the socket 29 at its concave (outer) surface.

Figure 25E:
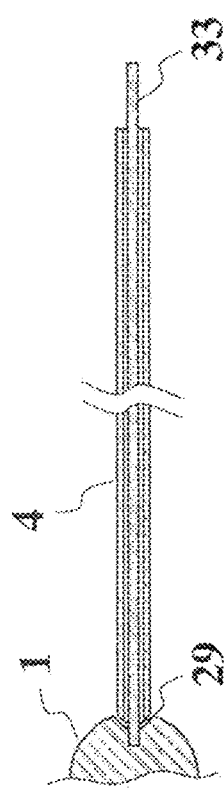

According to FIG. 25e the connecting element (shaft) 4 is pivotally connected to the intracorporeal unit 1. Here, the socket 29 has a convex shape wherein the cable 33 extending axially within the conduit of the shaft is connected at the socked 29 at its convex (inner) surface.

Figure 25F:
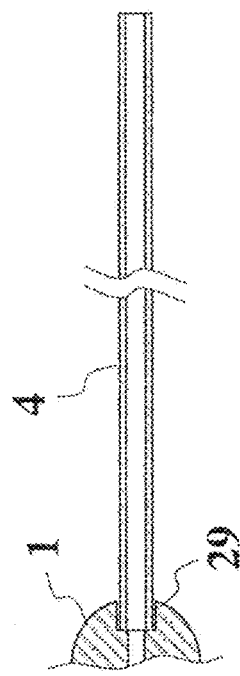

Another alternative design for a plug/socket connection is shown in FIG. 25f. Here, the connecting element (shaft) 4 is coupled with the intracorporeal unit 1 in a rigid manner, wherein the connecting element 4 is formed with an internal axial conduit. The intracorporeal unit 1 also comprises a conduit which is in fluid connection with the axial conduit of the connecting element 4. Thereby, a hydraulic/pneumatic circuit is formed between the extracorporeal unit and the intracorporeal unit for manipulating an actuator within the intracorporeal unit 1.

Figure 25G:
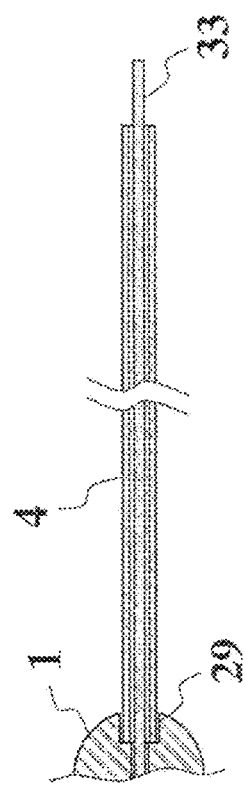

Finally, according to FIG. 25g the connecting element (shaft) 4 is coupled with the intracorporeal unit 1 in a rigid manner, wherein the connecting element 4 is formed with an internal axial conduit. The intracorporeal unit 1 also comprises a conduit which is in fluid connection with the axial conduit of the connecting element 4. Hereby, a hydraulic/pneumatic circuit is formed between the extracorporeal unit and the intracorporeal unit for manipulating an actuator within the intracorporeal unit 1. Additionally, a cable 33 is accommodated within the conduit of the connecting element 4 fixedly connected (in a detachable manner) with the intracorporeal unit 1 which cable 33 forms the inventive guide.

In that respect it has to be noted that the arrangement of a plurality of separate shafts spaced apart from each other in a substantially parallel manner has advantages over one single main trocar as used in the known prior art.

First, the use of a plurality of individual shafts allows the diameter of each shaft to be downsized to guarantee internal stability. This reduces the size of each incision needed in the body wall and, therefore, the operation load to the patient.

Second, by arranging a plurality of single shafts (at least two) substantially in parallel to each other, wherein each shaft is connected at its proximal end to the same extracorporeal unit and at its distal end to the same intracorporeal unit, a very stable, rigid design is created similar to a so-called tube frame.

Finally, because a large intracorporeal unit comprising the effector will only be introduced via a natural access into the body cavity, with the small sized shafts forming the mechanical and/or electrical and/or hydraulic connections between the extracorporeal unit and the intracorporeal unit, the advantages of the known prior art as designated above concerning the reduction of the patient's load and the advantages of a single main trocar concerning accuracy and handling can be brought together and a synergistic effect is created by the invention.

The present invention is not limited to the specific embodiments explained above. All possible combinations of features of the above embodiments are also considered to be covered within the scope of the present application.

The coupling member 5 can be regarded as the central member of the intracorporeal unit 1. The coupling member can be freely positioned within the body cavity by means of the connecting unit 2. For example, the intracorporeal device can be moved forward to target tissue by advancing the connecting unit 2 into the patient's body. In the same way, the intracorporeal unit 1 can be moved backwards, up, down, left and right.

For controlling the surgical manipulator 6, mechanical or electrical energy can be transferred from the extracorporeal unit 3 to the intracorporeal unit 1 via the connecting unit 2. For this purpose, the connecting unit 2 provides mechanical interconnection. Mechanical energy can be transmitted by movement of the connecting members 4 relative to each other, e.g. rotation, swivelling, translating, or by hydraulic or pneumatic pressure or flow. For transmission of hydraulic or pneumatic energy or flow, the connecting unit 2 may provide connecting members 4 having an internal axial conduit. Electrical energy can be transmitted via wires to actuators integrated in the intracorporeal unit 1. This transfer can be regarded as transfer of information between the extracorporeal unit 3 and the intracorporeal unit 1 via the connecting unit 2.

Other forms of energy can be transmitted from the extracorporeal unit 3 to the intracorporeal unit 1 via the connecting unit 2. These forms of energy can be photonic energy for illumination, for example, or electrical energy for powering high frequency cutters or driving light emitters for illumination. For this purpose, the connecting unit 2 provides electrical interconnection or interconnection able to transmit photonic energy. This transfer can be regarded as transfer of information between the extracorporeal unit 3 and the intracorporeal unit 1 via the connecting unit 2.

Control signals can be transmitted from the extracorporeal unit 3 to the intracorporeal unit 1 via the connecting unit 2. These control signals can be analog or digital electrical signals for controlling actuators or other means integrated in the intracorporeal unit 1 requiring external control. For this purpose, the connecting unit 2 provides electrical interconnection. This transfer can be regarded as transfer of information between the extracorporeal unit 3 and the intracorporeal unit 1 via the connecting unit 2.

Sensor signals can be transmitted from the intracorporeal unit 1 to the extracorporeal unit 3 via the connecting unit. These sensor signals can be analog or digital electrical signals and transmit image data from the camera system, status data from actuators, and sensor information from sensors e.g. about position of limbs, force exertion onto limbs, pressure exertion onto surfaces. For this purpose, the connecting unit 2 provides electrical interconnection. This transfer can be regarded as transfer of information between the extracorporeal unit 3 and the intracorporeal unit 1 via the connecting unit 2.

While the foregoing disclosure discusses illustrative embodiments, it should be noted that various changes and modifications could be made herein without departing from the scope of the described embodiments as defined by the appended claims. Accordingly, the described embodiments are intended to embrace all such alterations, modifications and variations that fall within scope of the appended claims. Furthermore, although elements of the described embodiments may be described or claimed in the singular, the plural is contemplated unless limitation to the singular is explicitly stated. Additionally, all or a portion of any embodiment may be utilized with all or a portion of any other embodiments, unless stated otherwise.

To the extent that the term "includes" is used in either the detailed description or the claims, such term is intended to be inclusive in a manner similar to the term "comprising" as "comprising" is interpreted when employed as a transitional word in a claim. Furthermore, the term "or" as used in either the detailed description or the claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

What is claimed is:

1. A surgical manipulator, comprising:
   an intracorporeal unit being completely arrangeable within a body cavity and comprising:
      a coupling member;
      an effector;
      at least one socket, wherein the at least one socket is firmly attached to the coupling member; and
      at least one guide, each guide comprising at least one tension wire having a first end and a second end, wherein the first end of the at least one tension wire is firmly attached to the at least one socket;
   an extracorporeal unit comprising a manipulator configured to manipulate at least the effector; and
   a connecting unit configured to connect the intracorporeal unit to the extracorporeal unit when the intracorporeal unit is arranged within the body cavity and configured to transfer information in the form of electro-mechanical control signals for controlling manipulating activity between said extracorporeal unit and the intracorporeal unit,
   wherein the connecting unit comprises rigid connecting members, formed by at least two separate shafts spaced apart from each other, said at least two separate shafts configured to be partly introduced into the body cavity through individual punctures created by the at least two separate shafts in a body wall, respectively, wherein each of the at least two separate shafts provides an electro-mechanical connection between the extracorporeal unit and the intracorporeal unit;
   the shafts having tip ends, configured to connect or dock to a respective socket of the intracorporeal unit and
   wherein the at least two separate shafts have an axial through hole or an axial groove through which a wire or cable is passed, wherein
   said wire or cable has a distal and a proximal end, wherein the distal end of the wire or cable has a first catching mechanism at its distal end configured to engage with the second end of the at least one tension wire.

2. The surgical manipulator according to claim 1, wherein the at least two separate shafts are spaced apart from each other in a substantially parallel manner.

3. The surgical manipulator according to claim 1, wherein the at least one guide is configured to bring said intracorporeal unit together with said connecting unit within the body cavity.

4. The surgical manipulator according to claim 1, further comprising:
a conveyor configured to convey said intracorporeal unit into the body cavity separately from the connecting unit; and
wherein the at least one guide is configured to bring said intracorporeal unit together with said connecting unit within the body cavity.

5. The surgical manipulator according to claim 1, wherein at least one of said at least two separate shafts of said connecting unit accommodates wires for transmitting energy and/or control signals from said manipulator of said extracorporeal unit to said intracorporeal unit to activate said effector.

6. The surgical manipulator according to claim 1, wherein at least one of said at least two separate shafts of said connecting unit accommodates wires, for transmitting sensor signals from the said intracorporeal unit to the said extracorporeal unit.

7. The surgical manipulator according to claim 1, wherein at least one of said at least two separate shafts of said connecting unit forms or accommodates transmission means for mechanically transmitting manual movements of said manipulator of said extracorporeal unit to said effector.

8. The surgical manipulator according to claim 1, wherein at least one of said at least two separate shafts of said connecting unit forms or accommodates an internal axial conduit for transmitting pressure or flow of a fluid to said intracorporeal unit.

9. The surgical manipulator according to claim 1, wherein said intracorporeal unit comprises a video camera.

10. The surgical manipulator according to claim 9, wherein said video camera is a stereoscopic camera.

11. The surgical manipulator according to claim 9, wherein at least one of said at least two separate shafts of said connecting unit accommodates wires, for transmitting at least one of energy and the control signals from said extracorporeal unit to said intracorporeal unit to activate said video camera.

12. The surgical manipulator according to claim 1, wherein said intracorporeal unit comprises an illuminator.

13. The surgical manipulator according to claim 12, wherein at least one of said at least two separate shafts of said connecting unit accommodates wires, for transmitting energy and/or control signals from said extracorporeal unit to said intracorporeal unit to activate the said illuminator.

14. The surgical manipulator according to claim 1, wherein said connecting unit comprises a plug at a distal end, the plug being fittably connectable with a socket of said intracorporeal unit.

15. The surgical manipulator according to claim 14, wherein said plug and said socket form at least one of a mechanical and electrical interconnection.

16. The surgical manipulator according to claim 1, wherein said connecting unit comprises cables shiftably accommodated within at least one of said at least two separate shafts and having at least one catch at free distal ends thereof, respectively, for catching said intracorporeal unit within the body cavity.

17. The surgical manipulator according to claim 16, wherein said connecting unit comprises a second catching mechanism at free distal ends thereof for catching said intracorporeal unit within the body cavity.

18. The surgical manipulator system according to claim 1, wherein the manipulator comprises at least one manual handle or at least one electrical actuator, said effector being controllable via the at least one manual handle or the at least one actuator.

19. The surgical manipulator according to claim 1, wherein the second end of the at least one tension wire of the intracorporeal unit has a second catching mechanism which correspond to the first catching mechanism provided at the distal end of the wire or cable passing through the axial through hole or groove of the at least one shaft.

20. The surgical manipulator system according to claim 1, further comprising a conveyor.

21. The surgical manipulator system according to claim 20, where the conveyor consists of an endoscope.

22. The surgical manipulator system according to claim 1, where at least one of the connecting members has a camera at a tip of the distal end which is introduced into the body cavity when connecting the connecting members with the intracorporeal unit.

23. The surgical manipulator system according to claim 1, where at least one of the connecting members has an illuminator at a tip of the distal end which is introduced into the body cavity when connecting the connecting members to the intracorporeal unit.

24. A method to connect an intracorporeal unit and a connecting unit of a surgical manipulator, the intracorporeal unit comprising a coupling member, an effector, at least one socket, wherein the at least one socket is firmly attached to the coupling member, and at least one guide, each guide comprising at least one tension wire having a first end and a second end, wherein the first end of the at least one tension wire is firmly attached to the at least one socket, the method comprising:
conveying said intracorporeal unit and the tension wires into a patient's body;
introducing at least two rigid connecting members of the connecting unit into the patient's body, the rigid connecting members comprising at least two separate shafts spaced apart from each other, said at least two separate shafts configured to be partly introduced into the body cavity through individual punctures created by the at least two separate shafts in a body wall, respectively, wherein each of the at least two separate shafts provides an electro-mechanical connection between an extracorporeal unit and the intracorporeal unit;
passing a catching wire through an axial through hole or groove of each of the connecting members, the catching wire having first catching mechanism at its tip end;
connecting or catching the second end of the tension wire with the first catching mechanism of the catching wire attached to the connecting member;
pulling back the catching wire so that the tension wire is pulled into the through hole or groove of the respective connecting member;
docking the connecting members at a respective socket of the intracorporeal unit; and
fixing the tension wires to maintain a docked state.

25. The method to connect the intracorporeal unit and the connecting unit according to claim 24 further comprising:
providing a second catching mechanism at a second end of the tension wire where the second catching mechanism is adapted to engage with the respective first catching mechanism of the catching wires of the connecting member.

26. The method to connect the intracorporeal unit and the connecting unit according to claim 25 further comprising:
introducing an endoscopic camera into patients body.

27. The method to connect the intracorporeal unit and the connecting unit according to claim 25 further comprising: introducing an illuminator into patients body.

\* \* \* \* \*